US009101783B2

(12) United States Patent
Troccaz et al.

(10) Patent No.: US 9,101,783 B2
(45) Date of Patent: Aug. 11, 2015

(54) MALODOR COUNTERACTING COMPOSITIONS AND METHOD FOR THEIR USE TO COUNTERACT SWEAT MALODOR

(75) Inventors: Myriam Troccaz, Saint-Julien-en-Genevois (FR); Sabine Beccucci, Eteaux (FR); Monica Bandera, Perroy (CH); Manuel Bourgaux, Echenevex (FR); Catherine Selig, Geneva (CH); Magali Lateulere, Geneva (CH); Anthony Clark, Manhattan, NY (US)

(73) Assignee: Firmenich SA, Geneva (CH)

( * ) Notice: Subject to any disclaimer, the term of this patent is extended or adjusted under 35 U.S.C. 154(b) by 239 days.

(21) Appl. No.: 13/319,411

(22) PCT Filed: Jun. 17, 2010

(86) PCT No.: PCT/IB2010/052736
§ 371 (c)(1),
(2), (4) Date: Nov. 8, 2011

(87) PCT Pub. No.: WO2010/146556
PCT Pub. Date: Dec. 23, 2010

(65) Prior Publication Data
US 2012/0052031 A1    Mar. 1, 2012

(30) Foreign Application Priority Data

Jun. 19, 2009    (WO) ................. PCT/IB2009/052634

(51) Int. Cl.
| *A61Q 15/00* | (2006.01) |
| *A61K 8/33* | (2006.01) |
| *A61K 8/34* | (2006.01) |
| *A61K 8/35* | (2006.01) |
| *A61K 8/36* | (2006.01) |
| *A61K 8/37* | (2006.01) |
| *A61K 8/49* | (2006.01) |

(52) U.S. Cl.
CPC . *A61Q 15/00* (2013.01); *A61K 8/33* (2013.01); *A61K 8/34* (2013.01); *A61K 8/342* (2013.01); *A61K 8/35* (2013.01); *A61K 8/361* (2013.01); *A61K 8/37* (2013.01); *A61K 8/4973* (2013.01); *A61K 2800/77* (2013.01)

(58) Field of Classification Search
CPC ....... A61K 8/33; A61K 8/361; A61K 31/201; A61K 31/202
See application file for complete search history.

(56) References Cited

U.S. PATENT DOCUMENTS

| 2,976,321 | A | * | 3/1961 | Dorsky et al. ................. 568/425 |
| 5,213,791 | A |   | 5/1993 | Lyon et al. ...................... 424/65 |
| 5,487,886 | A |   | 1/1996 | Lyon et al. ...................... 424/65 |
| 5,595,728 | A |   | 1/1997 | Brockett et al. ................. 424/65 |
| 5,649,979 | A |   | 7/1997 | Paget et al. ........................ 8/137 |
| 5,994,291 | A |   | 11/1999 | Aida et al. ......................... 512/8 |
| 6,060,043 | A |   | 5/2000 | Hayden et al. .................. 424/65 |
| 6,133,228 | A |   | 10/2000 | Pika et al. ........................ 512/21 |
| 6,218,355 | B1 |   | 4/2001 | Herrmann ....................... 512/27 |
| 6,369,026 | B1 |   | 4/2002 | Pika et al. ........................ 512/21 |
| 6,677,297 | B2 |   | 1/2004 | Frerot ............................. 512/20 |
| 7,723,286 | B2 |   | 5/2010 | Fehr et al. ......................... 512/8 |
| 7,935,669 | B2 |   | 5/2011 | Fehr et al. ......................... 512/1 |
| 2002/0037264 | A1 |   | 3/2002 | Burry et al. ..................... 424/65 |
| 2004/0102357 | A1 |   | 5/2004 | Smith et al. ...................... 512/3 |
| 2005/0233940 | A1 |   | 10/2005 | Perring et al. .................... 512/1 |
| 2006/0228250 | A1 | * | 10/2006 | Brown et al. ..................... 422/5 |
| 2007/0298994 | A1 |   | 12/2007 | Finke et al. ....................... 512/1 |
| 2008/0025935 | A1 |   | 1/2008 | Starkenmann et al. ......... 424/65 |
| 2010/0098650 | A1 |   | 4/2010 | Herrmann et al. .............. 424/65 |
| 2011/0288165 | A1 | * | 11/2011 | Bruheim et al. ............. 514/458 |

FOREIGN PATENT DOCUMENTS

| DE | 30 03 494 A1 | 8/1980 |
| EP | 0 829 463 A2 | 3/1998 |
| EP | 0 936 211 B1 | 8/1999 |
| EP | 0 971 021 A1 | 1/2000 |
| GB | 2 041 964 A | 9/1980 |
| WO | WO 95/04809 A1 | 2/1995 |
| WO | WO 95/08976 A1 | 4/1995 |
| WO | WO 98/47477 A1 | 10/1998 |
| WO | WO 99/60990 A2 | 12/1999 |
| WO | WO 01/28980 A1 | 4/2001 |
| WO | WO 03/049666 A2 | 6/2003 |
| WO | WO 2004/009051 A2 | 1/2004 |
| WO | WO 2004009051 A2 * | 1/2004 |
| WO | WO 2005/044206 A1 | 5/2005 |
| WO | WO 2006/079934 A2 | 8/2006 |
| WO | WO 2008/093272 A2 | 8/2008 |

OTHER PUBLICATIONS

CAS Registry No. 80-54-6 (Nov. 16, 1984).*
CAS Registry No. 18127-01-0 (Nov. 16, 1984).*
International Application No. PCT/IB2010/052736, Partial International Search Report dated Nov. 22, 2011.
Troccaz et al., "3-Methyl-3-sulfanylhexan-1-ol as a Major Descriptor for the Human Axilla-Sweat Odour Profile," Chemistry & Biodiversity, 1:1022-1035 (2004).
Troccaz et al., "Properties of Recombinant *Staphylococcus haemolyticus* Cystathionine β-Lyase (*metC*) and Its Potential Role in the Generation of Volatile Thiols in Axillary Malodor," Chemistry & Biodiversity, 5:2372-2385 (2008).

* cited by examiner

*Primary Examiner* — Bethany Barham
*Assistant Examiner* — Peter Anthopolos
(74) *Attorney, Agent, or Firm* — Winston & Strawn LLP

(57) ABSTRACT

The invention relates to a malodor counteractancy or counteracting (MOC) method that resorts to the use of specific malodor counteracting (MOC) mixtures of MOC ingredients. More particularly, the invention relates to new MOC compositions capable of neutralizing or masking in an efficient manner sweat malodor and which can be used in perfumes, deodorants, antiperspirants and other body care products.

12 Claims, 4 Drawing Sheets

FIGURE 1
a)
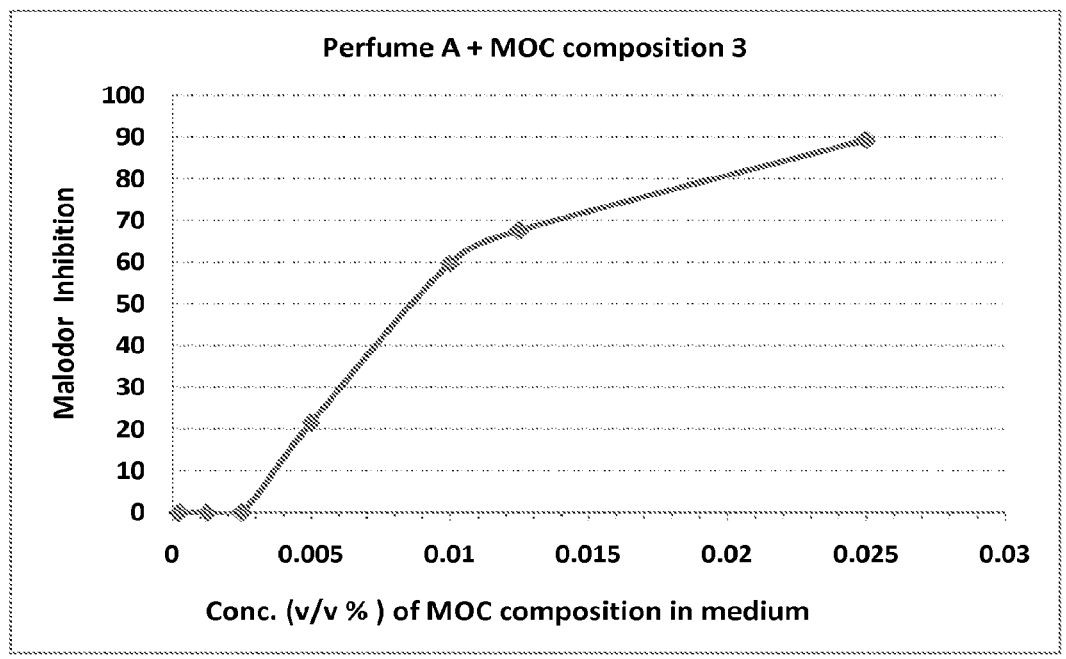
b)
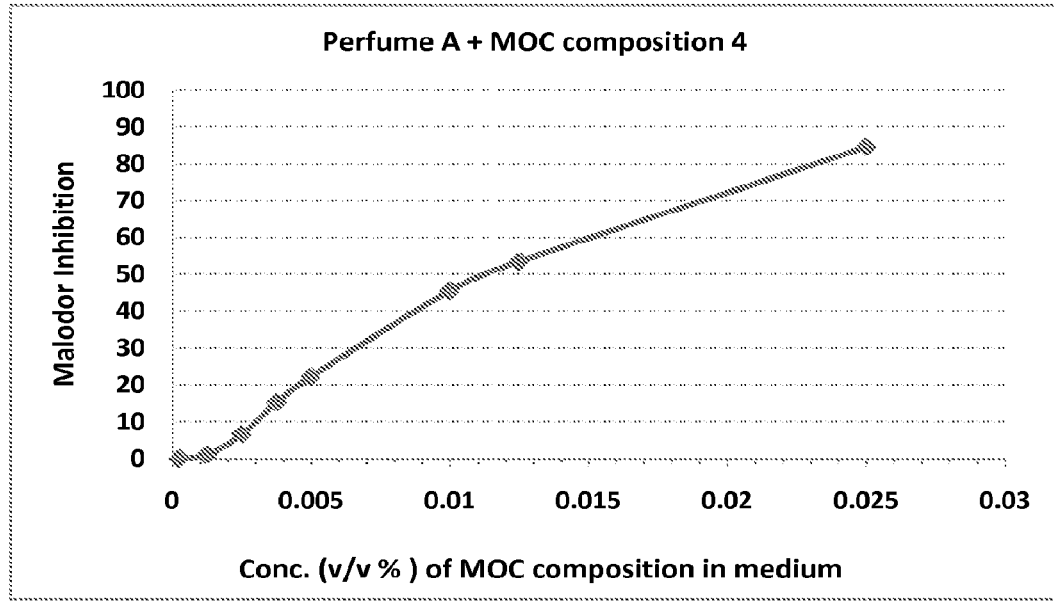

FIGURE 1 (continued)
c)
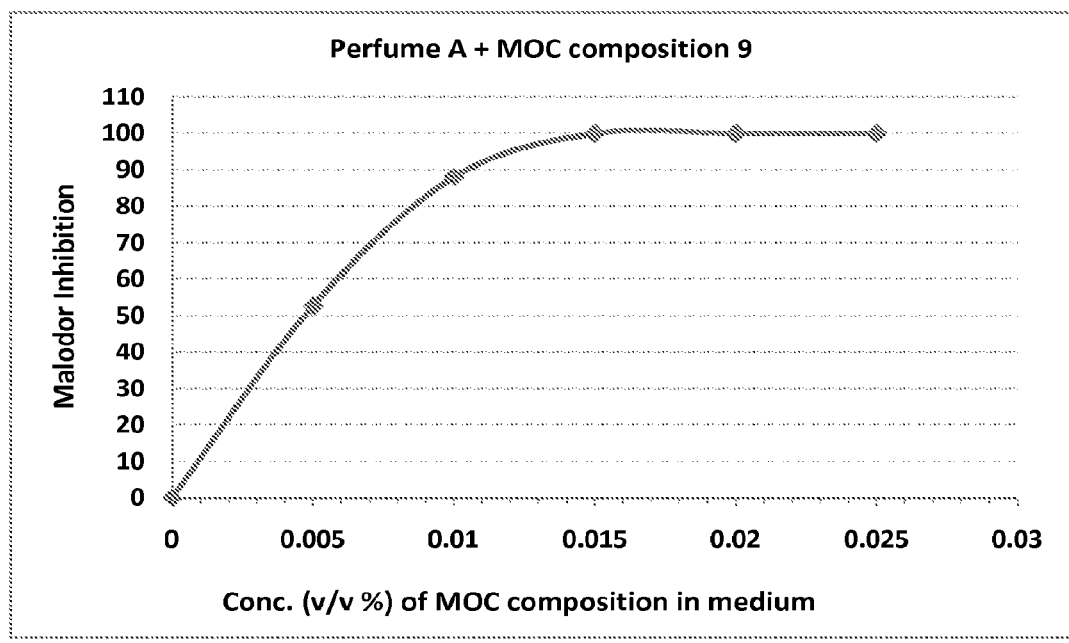
d)
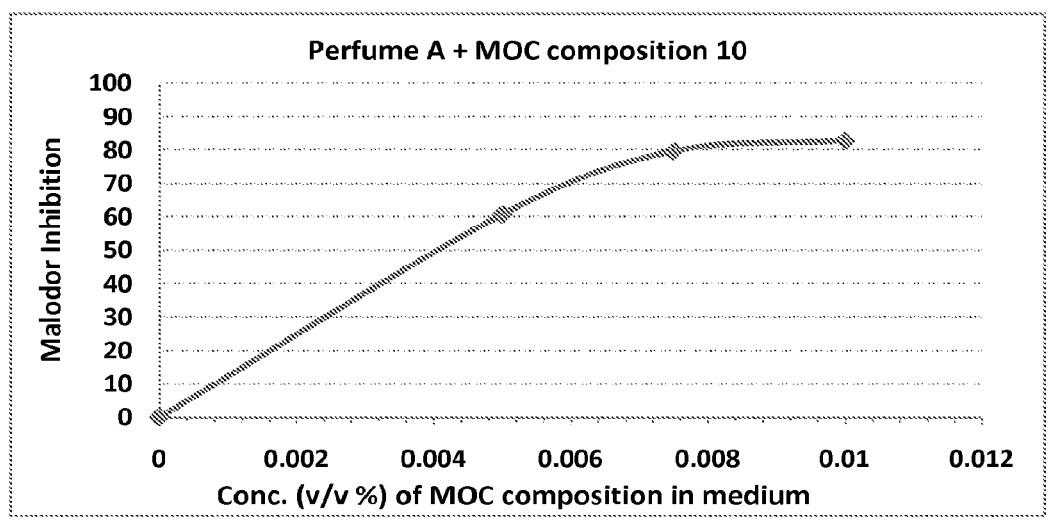

FIGURE 2
a)
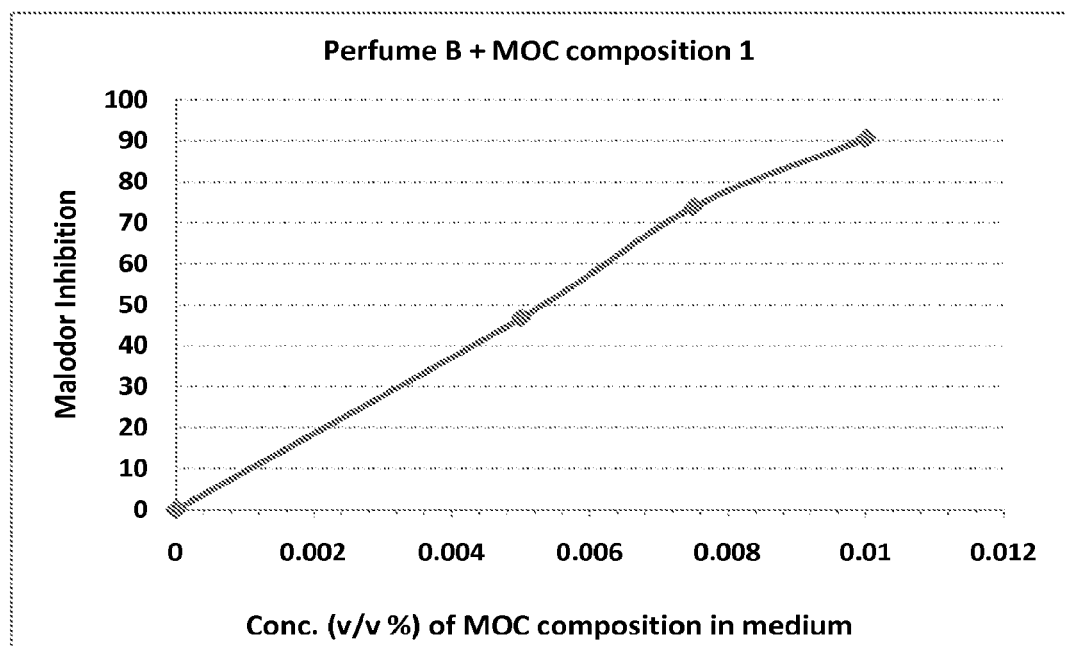
b)
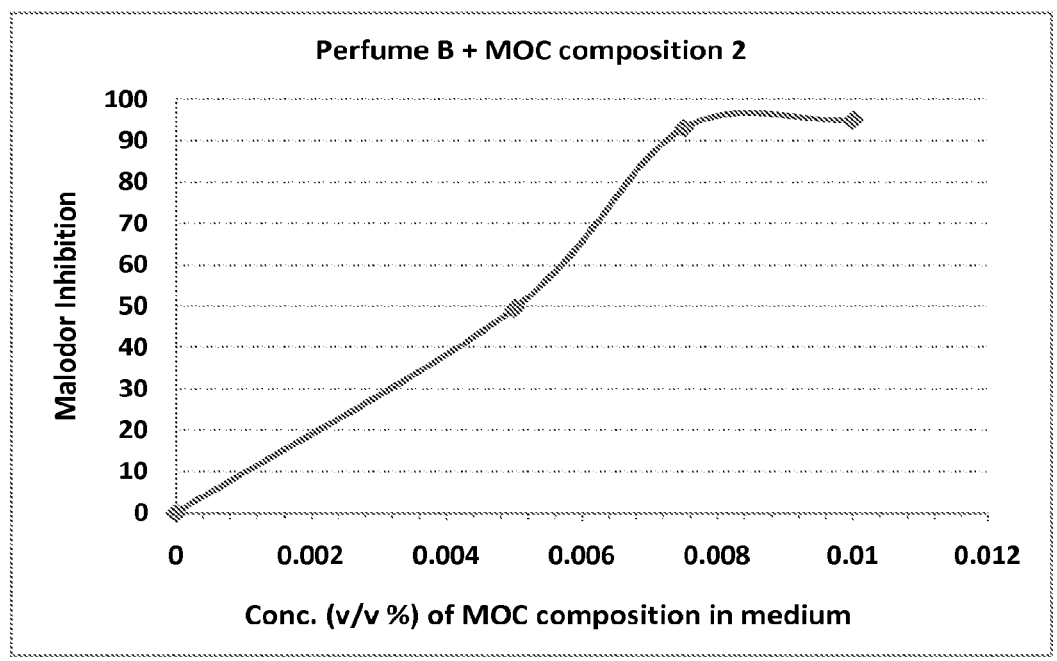

FIGURE 2 (continued)
c)
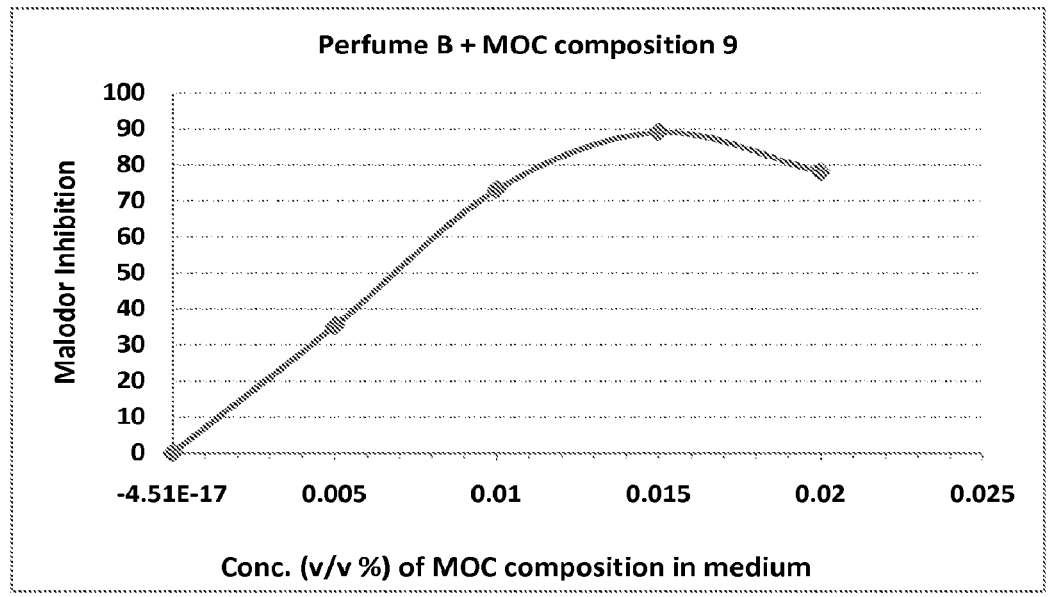
d)
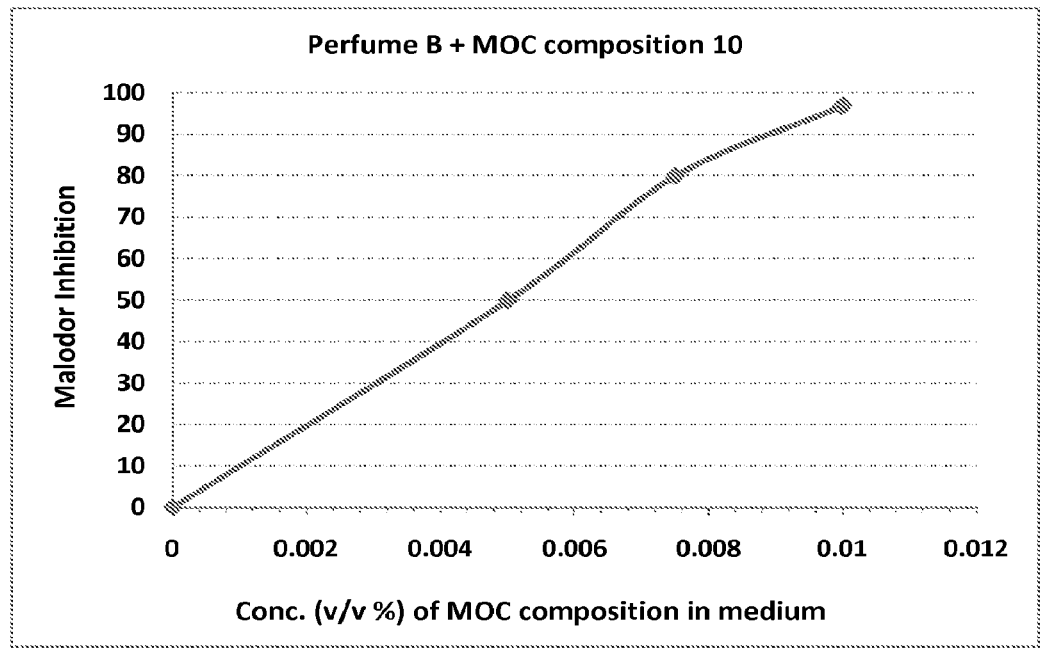

US 9,101,783 B2

MALODOR COUNTERACTING COMPOSITIONS AND METHOD FOR THEIR USE TO COUNTERACT SWEAT MALODOR

This application is a 371 filing of International Patent Application PCT/IB2010/052736 filed Jun. 17, 2010.

TECHNICAL FIELD

The present invention relates to a malodor counteracting (MOC) method that resorts to the use of specific malodor counteracting (MOC) mixtures of MOC ingredients, which act as deodorant or deodorizing compositions. More particularly, the invention relates to new deodorant or MOC compositions and consumer products containing them, namely perfumes, colognes, body sprays, deodorants and antiperspirants, capable of efficiently neutralizing or masking sweat malodor. The novel MOC compositions of the invention contain at least one effective MOC ingredient and are characterized by a malodor inhibition coefficient of at least 50%, at a defined composition concentration in an appropriate medium, against malodor generated by *Staphylococcus haemolyticus* enzymatic activity in said medium, together with a malodor reduction value of at least 2, relative to a maximum malodor score value of 5, measured under the same conditions but in the absence of the MOC composition.

The invention also relates to methods of use of the MOC compositions and of any finished consumer products containing them.

PRIOR ART

The prior art's richness in reports of methods to counteract and/or mask malodors, and more particularly sweat malodor, is such that a complete review of all the methods and compositions prior reported in this context is impossible here. It is clear however that there still exists a need to continue searching alternative ways of solving the sweat malodor problem, as evidenced by the constant publication of new methods of solving malodor occurrence.

In the field of sweat malodor counteraction, methods which resort to the use of compositions or products free from, or having a reduced content in, classical deodorant or antiperspirant ingredients, in particular aluminum or zirconium salts, well-known for their deodorant activity, are especially appreciated. The present invention aims at bringing a novel contribution in this context, by providing novel deodorant and antiperspirant compositions capable of counteracting, and more preferably suppressing, sweat malodor, whilst reducing or eliminating content in any such classical ingredients, and whilst also providing an efficient sensorial coverage of the malodor perceived by the user of such deodorant or antiperspirant products and/or of any other individuals present in the proximity of that user.

Although the prior art has previously reported a large variety of methods to identify ingredients and consumer products able to inhibit or reduce the occurrence of sweat malodor by interfering with the activity of axillary microorganisms responsible for generating such malodor, we have now surprisingly established that many such methods do not provide a full solution to the problem of inhibiting or suppressing sweat malodor.

For example, U.S. Pat. No. 5,213,791 discloses deodorant consumer products containing effective amounts of inhibitors of an amino acid β-lyase enzyme which contains the co-factor pyridoxal phosphate and catalyzes human body malodor, wherein the inhibitor is hydroxylamine or an aminoacid of formula $H_2N—O—CH(R)COOH$, R being hydrogen or a defined radical. Amongst the aminoacids of the latter formula, aminooxyacetic acid is preferred. Other documents in the same family, i.e. U.S. Pat. Nos. 5,595,728 and 5,487,886, further disclose inhibitors of specific formulae, as defined in the above documents. These prior art documents assume that sweat malodor is essentially generated by aminoacid β-lyase enzymes containing the pyridoxal phosphate co-factor and do not teach or suggest anything about inhibition of malodor resulting from the activity of enzymes which do not contain this co-factor and which generate sweat malodor through the cleavage of different precursors than those taught in these documents.

In a more recent document, U.S. Pat. No. 6,060,043, the malodor counteracting efficacy of some of the amino-acid derivatives taught in the above mentioned patent family have been put into doubt, and a novel solution based on the use of amino acids strictly in the D-form has been proposed.

Other efforts to attempt to provide valid solutions to the sweat malodor problem have relied on the increasing knowledge available on the nature of the chemical species thought to be responsible for the perception of sweat malodor and propose the use of specific chemicals as malodor standards to identify possible modulators of the malodor. One can cite in this context the contribution disclosed in US 2007/0298994, which relies on the use of 3-mercapto-3-methyl-hexan-1-ol as malodor standard. This compound had been reported a few years before as an important component of human sweat, and already proposed as a possible representative of the sulfury notes typical of sweat malodor, capable of serving as a malodor marker, but its use as a sensory marker as taught in the above-mentioned US application has not provided heretofore a quantitative solution to sweat malodor counteraction, very likely because the latter problem is more complex and cannot be solved through the sensory coverage of this compound's odor alone.

The present applicant has also provided a prior art contribution in WO 2006/079934, wherein there is described a method for screening compounds capable of inhibiting the malodor generated by the enzymatic activity of a variety of microorganisms, when the latter are put into contact with specific precursors as taught therein. A large amount of possible precursors is disclosed in this document, which also suggests a very large group of possible malodor inhibiting compounds, based on the structure of the precursors used, but gives no guidance as to the use of other malodor modulators, not structurally related to the precursor.

The present invention aims at providing a new and quantitative solution to the problem of sweat malodor reduction and more preferably suppression and inhibition thereof, by providing methods for the creation and use of specific and efficient malodor counteracting (MOC) compositions and products, which rely on specific combinations of ingredients presenting well-defined malodor counteracting parameters that we have surprisingly established as being essential to ensure efficient sweat malodor suppression. The present invention therefore provides an original and advantageous contribution to the solution of the sweat malodor problem.

SUMMARY AND DESCRIPTION OF THE INVENTION

The present invention relates to malodor counteracting (MOC) compositions able to at least reduce, and more preferably suppress, sweat malodor, comprising at least 30% by weight, relative to the weight of MOC composition, of at least one MOC ingredient, wherein the latter is characterized by a malodor inhibition coefficient of at least 25%, at a MOC ingredient weight per volume (w/v) concentration in an appropriate medium, against malodor generated by *Staphylococcus haemolyticus* enzymatic activity in said medium.

We have now surprisingly established that compositions containing such an ingredient or ingredients are capable of efficiently suppressing sweat malodor.

The parameters defining the MOC ingredients according to the invention are a result of the fact that we have surprisingly established that certain ingredients could effectively interfere with the bacterial activity on fresh sweat, so as to modify this activity in a manner making it possible to reduce or suppress the formation of malodor. Fresh sweat does not have a bad odor, but upon activity thereon of bacteria present on the skin, in particular on the axillary skin, certain precursors contained in the sweat generate malodorant metabolites. The MOC ingredients according to the invention, having a malodor inhibition coefficient of at least 25%, at a concentration of ingredient in the appropriate medium of at least 0.005% w/v, relative to the total volume of the medium, effectively interfere with such bacterial activity which is typically of an enzymatic nature, presenting a capacity to reduce or entirely suppress sweat malodor.

Compositions comprising one or more ingredients, and preferably at least three MOC ingredients, as defined above are preferred according to the invention. Even better performing MOC compositions according to the invention are those which comprise one or more ingredients characterized by a malodor inhibition coefficient of at least 30%, and preferably of 50% or more, at an ingredient concentration, in the appropriate medium, of at least 0.0125% w/v, relative to the volume of the medium.

As used herein, "a malodor counteracting (MOC) composition" is to be understood as a mixture of one or more MOC ingredients as defined above and which is capable of at least reducing the perception of malodor, i.e. of an odor that is unpleasant or offensive to the human nose.

According to the invention, the individual MOC ingredients, and their mixtures and compositions containing such MOC ingredients, as defined herein, can be used to reduce the malodor perceived from sweat, either as collected from individuals and used in a medium or surface which is not part of the human body, or in the form of sweat present on a sweated surface such as skin, hair or clothing, and as perceived by an individual or individuals in the vicinity of the malodor source.

By "a malodor inhibition coefficient" it is understood here a % inhibition value, relative to reference conditions, which is measured via a method essentially similar to that generally described in WO 2006/079934, more particularly on pages 8 and 11-15 of the above document, and in the examples thereof provided, and which requires that an ingredient to be screened be put into contact with bacterial cells of *Staphylococcus haemolyticus*, or with a β-lyase present in such cells, in the presence of a specific precursor of malodorant metabolites. The reference conditions correspond to 0% of malodor inhibition, i.e. to 100% generation of the malodorant metabolites under the screening conditions, in the absence of the MOC ingredient or composition.

The type of *Staphylococcus haemolyticus* strain suitable for use according to the invention is any one of the common strains of this bacterium which colonizes the human underarm region and has been found to efficiently release volatile sulfur compounds when put into contact with sweat or with a sulphur precursor typically present in fresh sweat. Useful such strains have been previously cited in WO 2006/079934, and many others can be used in the measurements according to the invention. The typical and preferred conditions of preparation of these bacteria strains are described in detail in this prior art document, and in the examples presented further on, wherein the specific *Staphylococcus haemolyticus* CNCM I-4170 strain has been used in the appropriate medium providing definition of the characterizing malodor inhibition coefficient for the ingredients and compositions according to the invention.

Further details of such a screening and % inhibition measurement and definition are described further on in this application. The precursor used, which may also be in the form of a human sweat sample, typically generates malodorant sulfur compounds when acted upon by the *Staphylococcus haemolyticus* cells, or by a β-lyase present in such cells. The malodor inhibition coefficient, as defined herein, reflects the % of reduction in free SH groups generated in the above-mentioned medium by the enzymatic activity of the bacterial cells when in presence of the MOC ingredient or MOC composition in question, as compared to the same measurement in their absence.

The concentration in free SH groups can be detected via commonly known methods, as described in WO 2006/079934, and in a more recent disclosure by M. Troccaz et al. in Chemistry and Diversity, 2008, vol. 5, pages 2372 to 2385, more particularly page 2384. A malodor inhibition coefficient of 30% for example, therefore means a capacity of the MOC ingredient to reduce by 30% the concentration of SH groups in the appropriate medium, as compared to the concentration thereof in the absence of said ingredient.

By an "appropriate medium" we mean here the medium wherein the appropriate precursor, and more preferably the Cys-Gly precursor exemplified further on, is put into contact with bacterial cells of *Staphylococcus haemolyticus*, under the generally known conditions described in WO 2006/079934, and to which the MOC ingredient or composition, as the case may be, is added to counteract the malodor generated by the bacterial or enzymatic cleavage of the precursor.

More specifically, by the "appropriate medium", in which the MOC ingredient presents the defined malodor inhibition coefficient, it is understood here a medium consisting essentially of a suspension of bacterial cells of *Staphylococcus haemolyticus* in a buffer, preferably 100 millimolar potassium phosphate (pH 7.5) buffer, also comprising a sulphur precursor of sweat malodor, preferably the Cys-Gly precursor S-[1-(2-hydroxyethyl)-1-methylbutyl]-L-cysteinylglycine, at a weight concentration of 0.17 millimolar (mM). Alternatively, the bacterial cells can be replaced by a β-lyase present in said cells.

The defined concentration of the MOC ingredient in the appropriate medium is understood here to mean a weight % concentration of at least 0.005%, relative to the volume of said medium (w/v %). More preferably, this concentration shall be at least 0.0125% w/v. Even more preferably, the MOC ingredient shall be present in the medium at a concentration of between 0.0125 and 0.05% or even 0.1% w/v, to provide a malodor inhibition coefficient of at least 30%, and more preferably above 50%, relative to the maximum malodor reference under the same conditions.

According to the invention, the MOC compositions may contain 50% by weight or more, relative to the weight of composition, of MOC ingredients.

According to preferred embodiments of the invention, the MOC compositions comprise at least 30% by weight of said MOC ingredient or ingredients, each of which is characterized by a malodor inhibition coefficient of at least 50% at a minimal concentration of 0.0125 w/v and more preferably 0.025%. The more active and preferred MOC ingredients for the MOC compositions of the invention shall be characterized by a malodor inhibition coefficient of 75% or more, at a concentration in the medium of at least 0.0125 or 0.0250 w/v, relative to the volume of the medium.

A second parameter possibly characterizing the MOC ingredients and compositions according to the invention, is a "malodor reduction value", which is understood here to be a value reflecting the perceived malodor reduction obtained in the presence of said MOC ingredient or composition, as compared to a reference value defined under similar conditions but in the absence of said ingredient or composition. The defined value is the result of a panel sensorial test and is defined on a scale of measurement wherein the reference value of maximum malodor perception (no malodor reduction at all) corresponds to 5.

It is therefore the difference between the maximum malodor perceived by a panel of evaluator individuals from the bacterial transformation of either sweat collected from human axilla, or of an appropriate precursor typically present in sweat, and the malodor perceived by the same evaluating panel from the same bacterial transformation, under similar conditions, but when the latter is carried out in the presence of the MOC ingredient or composition. Both the defined and the reference values are averaged values, statistically treated for standard deviation. A malodor reduction value of 2 for example means therefore that the malodor score attributed by the panel, on average, when the MOC ingredient or composition is applied to the sweat/bacteria containing sensory evaluation medium (or to the precursor/bacteria containing sensory evaluation medium), under controlled conditions, is reduced by 2 units relative to the reference value of the maximum sweat malodor perceived from the same medium, under the same conditions, when no MOC ingredient or composition is added thereto.

The sensory panel methods used for defining this malodor reduction value are described further on in the examples. They provide a sensory measure of the capacity of said ingredient or composition to effectively reduce the malodor perceived by the evaluators upon application of the compositions of the invention to sweated or sweat-containing media or surfaces.

By contrast, the malodor inhibition coefficient is an analytically determined value of the same capacity to reduce sweat malodor, but measured as a function of the concentration, in the appropriate medium, of metabolites resulting from the bacterial transformation of an appropriate precursor capable of generating said malodorant metabolites in the presence of *Staphylococcus haemolyticus*. We have now been able to establish that the MOC compositions of the invention which have a combination of these two parameters as described below provide unexpected efficacy against sweat malodor.

The MOC compositions according to the invention, which more preferably comprise at least three MOC ingredients as defined above, possess surprisingly useful malodor counteracting properties against sweat malodor and they are capable of masking, reducing, or even suppressing and/or neutralizing the latter, when applied to sweat collected from the axilla of individuals or to precursors present in such sweat. Moreover, they render consumer products such as perfumes, colognes and body sprays, or yet body deodorants and antiperspirants, to which they are added, particularly effective against malodor generated by body sweat.

MOC compositions wherein each of said MOC ingredients are characterized by a malodor inhibition coefficient of at least 50%, at an ingredient concentration of at least 0.0125% w/v in the appropriate medium and, amongst these, compositions comprising MOC ingredients characterized by at least 75% malodor inhibition coefficient are surprisingly advantageous and provide above 80% malodor reduction.

The malodor counteracting (MOC) compositions of the invention thus obtained are characterized by a malodor inhibition coefficient of about 40% or more, at a MOC composition volume/volume (v/v) concentration in the appropriate medium of at least 0.0125%, against malodor generated by *Staphylococcus haemolyticus* enzymatic activity in said medium. The malodor reduction value of such compositions is typically of at least 2, on the sensory scale wherein the maximum malodor reduction value, measured in the absence of the MOC composition, is 5. Moreover, amongst the latter, the MOC compositions of the invention which are characterized by a malodor inhibition coefficient of at least 50% against sweat malodor generated by the activity of a mixture of bacteria of *Staphylococcus haemolyticus* and a mixture of *Corynebacterium* spp. on human skin, or on sweat collected from human skin, preferably from the axillary area, provide advantageous consumer products against sweat malodor.

By a defined "MOC composition concentration" it is understood here a volume/volume concentration of at least 0.01%, relative to the volume of the sensory evaluation medium, defined as previously. More preferably, this concentration shall be at least 0.0125% v/v and preferably it will be comprised between 0.0125 and 0.05, or even 0.1% v/v, relative to the volume of the medium.

Preferred MOC compositions of the invention are also compositions wherein the MOC ingredients or ingredients are selected from the group consisting of: (−)-(2E)-2-ethyl-4-[(1R)-2,2,3-trimethyl-3-cyclopenten-1-yl]-2-buten-1-ol; 3-(4-tert-butylphenyl)propanal; 4-cyclohexyl-2-methyl-2-butanol; 3-(4-tert-butylphenyl)-2-methylpropanal; (+)-(1S,2S,3S)-2,6,6-trimethyl-bicyclo[3.1.1]heptane-3-spiro-2'-cyclohexen-4'-one; cashmeran (1,2,3,5,6,7-hexahydro-1,1,2,3,3-pentamethyl-4-indenone); 9,12-octadecadienoic acid, 9,12,15-octadecatrienoic acid, and mixtures thereof; nerolidol; 1,4-dioxacyclohexadecane-5,16-dione; 8,12-epoxy-13,14,15,16-tetranorlabdane; (−)-(1'R,E)-3,3-dimethyl-5-(2',2',3'-trimethyl-3'-cyclopenten-1'-yl)-4-penten-2-ol; (E)-2-dodecenal; 3-decanal, 2-methyldecanal and mixtures thereof; 8-isopropyl-6-methyl-bicyclo[2.2.2]oct-5-ene-2-carbaldehyde; 3-(3-isopropyl-1-phenyl)butanal; (E)-2-decenal; 3-(4-methyl-3-pentenyl)-3-cyclohexene-1-carbaldehyde, 4-(4-methyl-3-pentenyl)-3-cyclohexene-1-carbaldehyde and mixtures thereof; 9-undecenal; vetyver essential oil; vetyverone; 4,5,6,7,8,9,10,11,12,13-decahydrocyclododeca-1,3-oxazole; 2-tridecenal; 9-undecenal, 10-undecenal and mixtures thereof; nonanal; (+)-(4R)-1-p-menthene-9-carbaldehyde; (E)-4-decenal; 3,7-dimethyloctanal; eucalyptus essential oil; 3-(3,3-dimethyl-5-indanyl)propanal, 3-(1,1-dimethyl-5-indanyl)propanal and mixtures thereof; (Z)-4-dodecenal; 3-(6,6-dimethyl-bicyclo[3.1.1]hept-2-en-2-yl) propane; and mixtures of two or more of the preceding ingredients.

Sweat malodor counteracting compositions comprising at least 30% by weight, relative to the total weight of the composition, of ingredients selected from the group above-defined are preferred.

Amongst the latter, embodiments of the compositions in which at least 50% by weight of the MOC composition is formed of 9,12-octadecadienoic acid, 9,12,15-octadecatrienoic acid, or mixtures thereof, provide excellent malodor counteracting products, particularly when they further comprise from 5 to 30% by weight of 3-(4-tert-butylphenyl)propanal.

Typically, any particular embodiments of the MOC compositions of the invention, characterized by at least 60% malodor inhibition coefficient, at a composition concentration of at least 0.0125% v/v in the appropriate medium, against malodor generated by *Staphylococcus haemolyticus* enzymatic activity in said medium, and a malodor reduction value of at least 2, and preferably 3 or 4, provide prime embodiments of the MOC compositions.

All the MOC compositions of the invention, in particular embodiments, may be essentially or entirely formed, i.e. contain more than 50% by weight, or be formed essentially of 100% by weight of MOC ingredients, the latter being defined as previously anywhere in this description. This means therefore that the MOC compositions may "consist" (contain 100% by weight of) said MOC ingredients.

Specific examples of embodiments of MOC compositions according to the invention are presented further on.

The MOC compositions of the invention are particularly useful for the preparation of consumer products capable of reducing or suppressing the body malodor generated by sweating, to which they are added in a generally known manner and in concentrations which are dependent of the MOC activity of said composition and of the nature of the consumer product into which the latter is incorporated. The invention therefore also relates to such consumer products, of which perfumes, colognes and body sprays are particular examples, as they are typically used by the consumer to provide a pleasant scent to skin and hair in particular. Of course, such perfuming compositions may also be used to spray textiles for example, in particular clothes and other body and hair wear textiles, which can acquire malodor through the user's sweating, so as to possibly prevent the development of malodor from textiles carrying fresh sweat and small amounts of skin bacteria.

As "perfuming compositions" according to the invention it is understood here compositions which are distinct from the MOC compositions previously defined (formed of only MOC ingredients). The perfuming compositions typically contain the MOC composition together with a perfuming co-ingredient, a solvent or an adjuvant or carrier of current use in perfumery, or a mixture of two or more of the latter.

The MOC composition may be used in the perfuming compositions in a large variety of concentrations, comprised between 10 and 80% by weight of the weight of perfuming composition, and more preferably of at least 20% by weight of the latter's total weight.

Preferred embodiments of the perfuming compositions of the invention, namely perfumes, colognes, body sprays, may comprise from 40 to 60% by weight of MOC composition as defined previously.

A perfuming composition which has a malodor inhibition coefficient of at least 60%, measured at a defined perfuming composition concentration in the appropriate medium, against malodor generated by *Staphylococcus haemolyticus* enzymatic activity in said medium, and a malodor reduction value of at least 3, is also an object of the present invention.

By a defined "perfuming composition concentration" it is understood here a concentration of at least 0.02% v/v, and more preferably comprised between 0.025 and 0.05% v/v, relative to the volume of the medium.

To provide the desired MOC effects to counteract sweat malodor, a MOC ingredient can be used on its own, more preferably in the form of the above-defined MOC compositions, or yet in the form of the perfuming compositions containing in particular perfuming co-ingredients, meaning other ingredients added mainly for their perfuming effect. Therefore, the perfuming compositions of the invention comprise at least two distinct components, the MOC composition of the invention and a mixture of fragrance ingredients typically of a different nature and which are essentially intended to provide a desired hedonic effect of a pleasant nature.

By a "perfuming co-ingredient" it is meant here a compound of current use in perfumery, which is used in perfuming a composition or consumer product, to impart a pleasant odor thereto. In other words, such a co-ingredient must be recognized by a person skilled in the art as being able to impart or modify, in a positive or pleasant way, the odor of a composition, and not just as having an odor.

The nature and type of the perfuming co-ingredients of the MOC composition in the perfumes and perfuming compositions of the invention do not warrant a more detailed description here, which in any case would not be exhaustive, the skilled person being able to select them on the basis of its general knowledge and according to intended use or application and the desired perfuming effect. In general terms, these perfuming co-ingredients belong to chemical classes as varied as alcohols, aldehydes, ketones, esters, ethers, acetates, nitriles, terpene hydrocarbons, nitrogenous or sulfurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, and in other works and textbooks of a similar nature, as well as in the abundant patent literature in the field of perfumery. It is also understood that said co-ingredients may also be compounds known to release in a controlled manner various types of perfuming compounds, either through chemical reaction cleavage of chemical bonds of heavier precursors or through physical release of such perfuming compounds, for example when the latter are encapsulated or carried in emulsion, microemulsion and/or nanoemulsion type perfume carrier system.

As liquid carriers for such perfuming ingredients or as components of the perfuming compositions of the invention, one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as di-propylene glycol, diethyl phthalate, isopropyl myristate, benzyl benzoate, 2-(2-ethoxyethoxy)-1-ethanol or ethyl citrate, which are commonly used. Others, having an equivalent function of solubilizing the MOC compositions and their perfuming co-ingredients, are equally adapted to be used in the perfuming compositions of the invention.

The perfuming co-ingredients, as well as the MOC ingredients and compositions of the invention, used to prepare the perfuming compositions, and consumer products such as body deodorants and antiperspirants, may also be present in a solid form, encapsulated or dispersed in solid carriers. As appropriate solid carriers one may cite, as non-limiting examples, absorbing gums or polymers, or yet encapsulating materials. Examples of such materials may comprise wall-forming and plasticizing materials, such as mono, di- or tri-saccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- and Gehermittel in Lebensmittel, Band 2 der Schriftenreihe Lebensmittelchemie, Lebensmittelqualität, Behr's Verlag-GmbH & Co., Hamburg, 1996 and other textbooks in the art of encapsulation or entrapment of compounds and compositions such as perfumes, flavors and pharmaceuticals.

Encapsulation is a well known process to a person skilled in the art, and may be performed, for instance, using techniques such as spray-drying, agglomeration or yet extrusion; or it may also consist of a coating encapsulation method, including coacervation and complex coacervation techniques, core shell encapsulation methods, etc. Provided that the encapsulation system does not negatively affect the MOC activity and efficacy of the MOC compositions, or of the perfuming compositions of the invention, any type of delayed release system carrier, providing for physical release of the entrapped materials, is adapted as a carrier for the MOC and perfuming ingredients and compositions as defined herein.

Preferred encapsulates of the MOC ingredients and compositions of the invention, and of the perfuming co-ingredients, which can be used in the perfuming compositions and other consumer products cited above, are the microcapsule systems commercialized by Firmenich SA (Switzerland) under the tradenames Fircaps® and PopScent® for example, based respectively on modified starch and melamine resin or polyurea type carriers.

The MOC and perfuming ingredients may also be used in the form of chemical release systems, i.e. heavier molecules which are capable of releasing the MOC ingredient and/or perfuming ingredient by chemical cleavage under the conditions of use—many such chemical release systems have been disclosed in the prior art, namely in the patent literature, which release the MOC ingredient via hydrolysis, photolysis or other such reaction mechanisms. One may cite in this context prior art documents such as for example WO 95/04809, EP 0971021, WO 03/049666, EP 0936211, WO 99/60990, WO 01/28980, WO 08/093272, WO 98/47477, US 2004/0102357, DE 3003494 and WO 95/08976, provided that such chemical release systems, under the conditions of their application, allow the release of the corresponding active MOC ingredient.

It goes without saying that, provided the encapsulation or chemical release technologies for delayed release of an ingredient or composition in application, does not interfere with the capacity of said ingredient or composition to fulfill the objective of the present invention, i.e. the reduction or suppression of sweat malodor, particularly in axillar skin, any combination thereof with the present invention malodor counteraction technology is appropriate to provide composition embodiments of the invention as presently disclosed and claimed.

As mentioned above, consumer products containing the MOC compositions or the perfuming compositions of the invention, such as body deodorants and antiperspirants, are also an object of the present invention. The nature of such products can be any and is well-known to the person skilled in the art of cosmetics and products for body and hair care in particular. These consumer products are commonly perfumed and the MOC compositions of the invention can be added thereto as such, or as components of the perfuming compositions of the invention.

Such consumer products typically comprise a consumer product base, in addition to the MOC and/or perfuming composition of the invention.

For the sake of clarity, by "consumer product base" we mean here a base which is distinct from, but compatible with, the MOC and perfuming compositions of the invention, and which is typically formed of substances capable of achieving the functional effect required typically from that product, such as freshening, deodorizing and odor neutralizing. Typical consumer product bases are the functional mixtures of ingredients that form the base of for example a body care preparation such as a body deodorant or antiperspirant. The latter may assume any form that is current, such as for example the form of a cream, gel, spray, pump-spray or aerosol, or yet stick. Such deodorants and antiperspirants are very well-known to the cosmetic specialist and the choice of their ingredients and forms does not require any particular effort beyond the general skill of the practitioner in the art of cosmetics and particularly body deodorants and antiperspirants.

Thus the nature and type of the constituents of the consumer product base do not warrant a more detailed description here, which in any case would not be exhaustive, the skilled person being able to select them on the basis of its general knowledge and according to the nature and the desired effect of said product. Merely as examples of appropriate such bases, representative of deodorant and antiperspirant consumer products, one can cite in this context prior art documents such as U.S. Pat. No. 6,060,043 and US 2002/037264. The latter describe in detail the types of ingredients, and their concentration and function, which are common in such consumer product bases. Of course, many other prior art documents can be found which detail appropriate deodorant and antiperspirant bases in particular, into which the MOC compositions and perfuming compositions of the invention can be incorporated to provide a sweat malodor counteraction effect.

Some of the above-mentioned consumer product bases may represent aggressive media for the MOC or perfuming compositions of the invention, so that it may be necessary to protect the latter from premature decomposition, for example by encapsulation as previously mentioned.

The proportions in which the MOC compositions, or the perfuming compositions containing them, can be incorporated into the various aforementioned consumer products may vary within a wide range of values. These values are dependent on the nature of the product as well as on the desired malodor counteracting effect that one wants to achieve. In many of these consumer products, the amount of perfuming composition containing the MOC component that is typically added to the consumer product is comprised between 0.01 and 10%, more preferably of at least 0.5%, and even more preferably between 1 and 5%, by weight, of MOC or perfuming composition according to the invention, relative to the total weight of the consumer product. More common ranges are comprised between 0.05 and 5% by weight, or yet from 0.1 to 3% and more preferably between 0.3 and 2% by weight, relative to the weight of the deodorant or antiperspirant in which the compositions are incorporated.

A body deodorant or antiperspirant which has a malodor inhibition coefficient of at least 60%, measured at a concentration of at least 0.5% v/v of said deodorant or antiperspirant in the appropriate medium, against malodor generated by *Staphylococcus haemolyticus* enzymatic activity in said medium, and a malodor reduction value of at least 3, and more preferably 4, is also an embodiment of the invention.

According to another embodiment of the invention, there is provided a method to counteract sweat malodor, wherein there is applied to sweat, to a sweat-generating surface, or to a sweat-carrying surface, a malodor counteracting (MOC) composition as previously defined, in a form and amount appropriate and sufficient to reduce, mask, eliminate or prevent any sweat malodor perception by an individual exposed to the sweat or to said surface. Preferably, the MOC composition is applied to human skin or hair, and preferably to the human axillary skin. Any embodiment of the MOC composition, perfuming composition, or perfumed product previously described in this disclosure, is appropriate for use according to this method.

Embodiments of the method of the invention comprise methods wherein the MOC composition or perfuming composition of the invention is applied in the form of a perfuming composition, namely a perfume, a cologne, or in the form of a body deodorant or antiperspirant.

BRIEF DESCRIPTION OF THE DRAWINGS

FIGS. 1 a) to d) show the % malodor inhibition effectiveness of a reference Perfume A to which the MOC compositions of the invention described in Examples 1 to 10 were added in a variety of concentrations, as a function of the perfume's capability to reduce the malodor of sulfur-like smelling compounds generated according to the testing Protocol A. (Example 15).

FIGS. 2 a) to d) show the % malodor inhibition effectiveness of a reference Perfume B to which the MOC compositions of the invention described in Examples 1 to 10 were added in a variety of concentrations, as a function of the perfume's capability to reduce the malodor of sulfur-like smelling compounds generated according to the testing Protocol A. (Example 16).

FIG. 7 shows the malodor counteraction effectiveness of MOC composition 9, at various weight % concentrations in the AP base described in Example 18, as measured via the panel sensory method described in Example 17.

EXAMPLES

Figure 3:
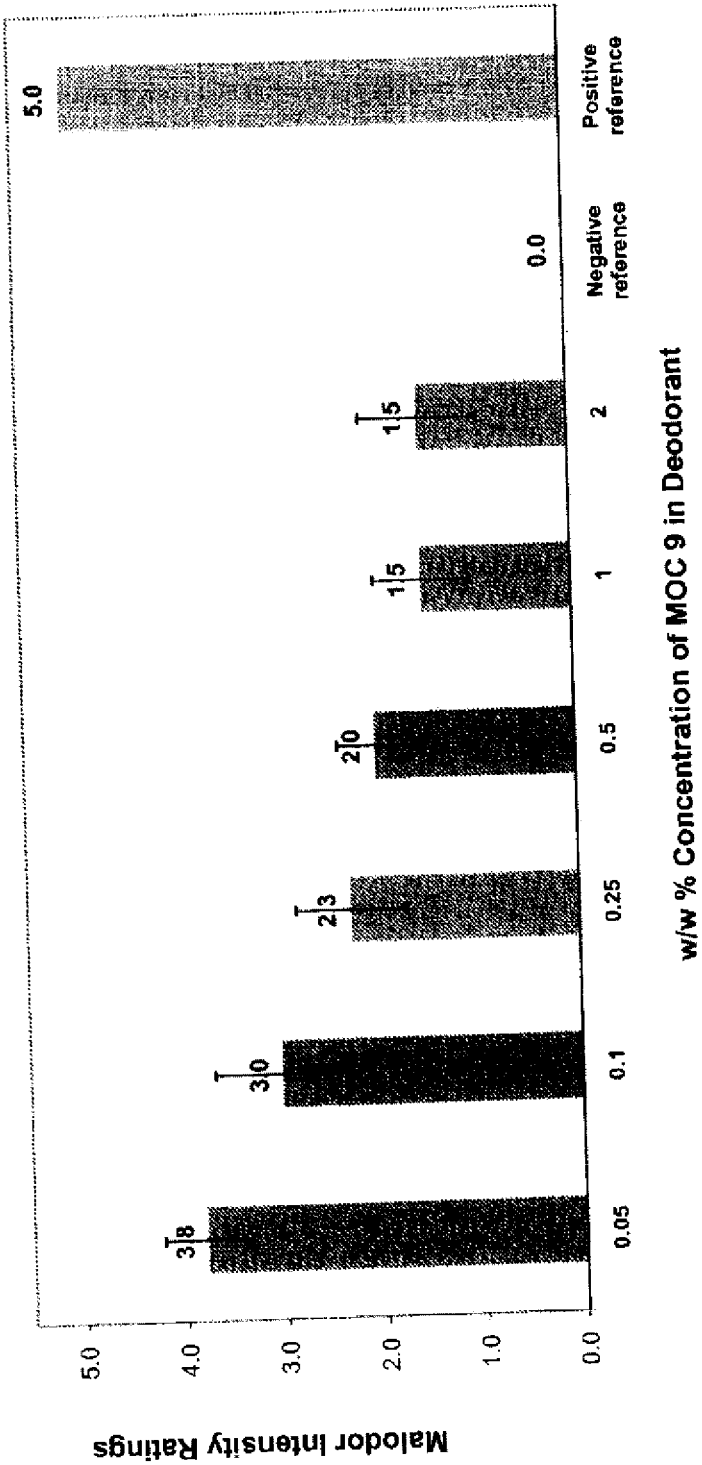
FIG. 3 shows the malodor counteraction effectiveness of a spray deodorant product comprising MOC composition 9 of the invention, as measured via the panel based sensory method described in Example 17 as Protocol B.

The invention will now be described in further detail by way of the following examples.

Examples 1 to 14

Malodor Counteracting (MOC) Compositions and Their Use to Reduce Perception of Sweat Malodor A number of malodor counteracting compositions according to the invention were prepared by admixture, in the proportions indicated, of the MOC ingredients listed in Tables 1 and 2. The latter also summarize the ability of each of said ingredients to reduce sweat malodor, as evidenced by the respective malodor inhibition coefficient indicated for each ingredient. These values were measured via the method indicated hereafter, designated as Protocol A.

Protocol A. In-Vitro Malodor Inhibition of Individual MOC Ingredients—General Conditions of Evaluation A Cys-Gly precursor, S-[1-(2-hydroxyethyl)-1-methylbutyl]-L-cysteinylglycine, is subject to enzymatic transformation both in the absence (blank test) and in the presence of each MOC ingredient. Detection of enzymatic activity inhibition is measured via the sulfur groups, namely thiol groups, freed from the precursor bacterial transformation, by comparison with the reference experiment in the absence of the respective MOC ingredient, said sulfur groups being detected by interaction with DTNB, a known chemical detector system for thiols. The reaction can be monitored by absorbance reading at 412 nm. The procedure can be performed indifferently with either a purified or semi-purified enzyme or intact bacterial cells, as in the case described here. Malodor inhibition coefficient is measured as a function of the percentage of free thiol groups in the medium, over time, by an absorbance method, and reflects the reduction in malodor obtained in the presence of the MOC ingredients and compositions.

Reagents and Equipment

Preparation of Bacterial Suspension

*Staphylococcus haemolyticus* CNCM I-4170 was grown under generally known conditions in Brain-Heart Infusion plus 0.5% of Tween® 80. At the end of the growth phase, the bacterial cells were harvested by centrifugation at 5000 rpm for 15 min. The cell pellet was then washed with 0.1 volumes of sterile potassium phosphate buffer 0.1 M, pH 7.5. Cell pellets were finally concentrated 5 times in the same buffer. 0.25 Volumes of this suspension were then added to each sample to be tested, to a final volume of 200 µl.

Preparation of the Cys-Gly Precursor (Enzyme Substrate)

Cys-Gly-precursor (MM=292.1 g/mole), prepared as described in WO 2006/079934, was dissolved at 0.25 mg/ml in potassium phosphate buffer 0.1 M, pH=7.5, leading to a 0.86 mM solution. The precursor was used at 0.17 mM final concentration.

Detection Reagent DTNB

DTNB (5,5'-Dithio-bis-(2-nitrobenzoic acid; MM=396.36 g/mol) was prepared at 3.9 mg/ml (equivalent to 10 mM) in potassium phosphate buffer 50 mM, pH=7.5+0.1 mM EDTA. The reagent was used at 0.5 mM final concentration.

Reader Type:

Standard absorbance reader.

Liquid Handling:

Manual or automatic handling using a conventional robotic station.

General Procedure: reagents are admixed, and the reaction is started by adding the bacterial cell suspension as the last reagent.

Absorbance measurements, over time and relative to a blank, were taken, the final volume of each sample having been kept constant at 200 ml.

As is apparent from the Tables 1 and 2, the MOC ingredients according to the invention were active against sweat malodor in a range of concentrations varying from about 0.001 to 0.1% w/v, relative to the volume of the appropriate medium. Preferred activities were observed in a range of concentrations between 0.005 and 0.1% w/v.

Following this same procedure indicated above, but using instead of the individual ingredients the fourteen MOC compositions according to the invention listed in Tables 1 and 2, we established that each such composition was capable of providing the malodor reduction effect indicated in the results summarized in Tables 3 and 4.

As the results in Tables 3 and 4 show, the MOC compositions of the invention, which comprised at least 40% by weight, and in many cases 80% or more, of MOC ingredients according to the invention, when used at a concentration of at least 0.01% v/v relative to the total volume of the test medium, provided malodor inhibition coefficients representing a malodor reduction of at least 50%, relative to the activity of the reference, and even at lower concentrations were still able to provide an efficient malodor counteracting effect.

The compositions of the invention effectively reduced sweat malodor when used in a range of concentrations of between 0.006 and 0.025% v/v, relative to the appropriate medium volume, and had essentially suppressed all malodor at this higher range limit value of concentration.

TABLE 1

| MOC INGREDIENT | Ingredient Malodor Inhibition Value (%) Concentration in Medium (w/v %) | | | | | | | | MOC COMPOSITIONS 1  2  3 (Ingredient concentration w/w %) | | |
|---|---|---|---|---|---|---|---|---|---|---|---|
| | 0.0006 | 0.0012 | 0.0025 | 0.006 | 0.0125 | 0.025 | 0.05 | 0.1 | 1 | 2 | 3 |
| (−)-(2E)-2-Ethyl-4-[(1R)-2,2,3-trimethyl-3-cyclopenten-1-yl]-2-buten-1-ol [1] | | 0.00 | 21.16 | 70.79 | 79.96 | 80.33 | | | 6.00 | | |
| Bourgeonal [2] | | 4.15 | 7.06 | 42.61 | | | | | 2.70 | | |
| Coranor ® [3] | | 0.00 | 0.00 | 10.83 | 49.78 | 77.73 | 77.76 | | | | |
| Lilial ® [4] | | 0.90 | 9.47 | 37.51 | 80.98 | 89.99 | | | 7.70 | 3.50 | 58.00 |
| (+)-(1S,2S,3S)-2,6,6-Trimethyl-bicyclo[3.1.1]heptane-3-spiro-2′-cyclohexen-4′-one [1] | | 0.00 | 14.02 | 26.00 | 72.64 | 75.94 | 75.68 | | | | |
| Cashmeran | | 0.00 | 0.00 | 19.17 | 54.04 | 71.46 | 70.07 | 73.15 | | 0.60 | |
| Mixture of 9,12-octadecadienoic acid & 9,12,15-octadecatrienoic acid | 54.35 | 69.63 | 79.57 | 84.91 | 100 | 100 | | | 32.00 | 47.00 | |
| Nerolidol | | 0.00 | 6.52 | 53.50 | 56.88 | 68.45 | 66.85 | | | | |
| 1,4-Dioxacyclohexadecane-5,16-dione [1] | | 0.00 | 0.00 | 0.00 | 28.18 | 37.31 | 36.48 | | 3.00 | | |
| Tetrahydromyrcenol | | 0.00 | 0.00 | 0.00 | 0.00 | 41.38 | 72.56 | 66.63 | | | |
| Ambrox ® [5] | | 0.00 | 0.00 | | | 18.23 | 38.00 | 0.30 | | | |
| Terpenyl acetate | | 0.00 | 0.00 | 0.00 | 0.00 | 6.81 | 00.00 | 46.00 | 47.00 | 12.00 | |
| 4-tert-Butyl-1-cyclohexanol | | 0.00 | 0.00 | 0.00 | 0.00 | 59.78 | 89.12 | | | | |
| Clove absolute | | 0.00 | 0.00 | 0.00 | 0.00 | 14.00 | 100.00 | | 0.60 | | |
| (−)-(1′R,E)-3,3-Dimethyl-5-(2′,2′,3′-trimethyl-3′-cyclopenten-1′-yl)-4-penten-2-ol [1] | | 0.00 | 27.39 | 75.11 | 76.95 | 76.65 | | | 0.60 | | |
| Essential cedar oil | | 0.00 | 0.00 | 11.23 | 17.00 | 20.00 | | | 1.50 | | |
| 3,5,5-Trimethyl-1-hexanol | | 0.00 | 0.00 | 0.00 | 0.00 | 34.95 | 58.33 | 62.93 | | | |
| Cardamome essential oil | | 0.00 | 0.00 | 0.00 | 25.06 | | | | | 0.60 | |
| Orange terpenes | | 0.00 | 0.00 | 0.00 | 0.00 | 32.10 | | | 0.30 | | |
| Patchouli essential oil | | | | 17.51 | | | | | | | 29.00 |

| MOC INGREDIENT | MOC COMPOSITIONS | | | | | | |
|---|---|---|---|---|---|---|---|
| | 4 | 5 | 6 | 7 | 8 | 9 | 10 |
| | (Ingredient concentration w/w %) | | | | | | |
| (−)-(2E)-2-Ethyl-4-[(1R)-2,2,3-trimethyl-3-cyclopenten-1-yl]-2-buten-1-ol [1] | 6.00 | 6.00 | | | | | |
| Bourgeonal [2] | | | | | | | |
| Coranor ® [3] | | | 10.00 | | | 13.00 | |
| Lilial ® [4] | 64.00 | 29.00 | 10.00 | | | | |
| (+)-(1S,2S,3S)-2,6,6-Trimethyl-bicyclo[3.1.1]heptane-3-spiro-2′-cyclohexen-4′-one [1] | | | | | | | 4.00 |
| Cashmeran | | | | | | | |
| Mixture of 9,12-octadecadienoic acid & 9,12,15-octadecatrienoic acid | | | 30.00 | 33.00 | 38.00 | 38.00 | 30.00 |
| Nerolidol | | | | 11.00 | 25.00 | | 35.00 |
| 1,4-Dioxacyclohexadecane-5,16-dione [1] | | 24.00 | 5.00 | 11.00 | 13.00 | 13.00 | |
| Tetrahydromyrcenol | | | 10.00 | | | | |
| Ambrox ® [5] | | | | | | | |
| Terpenyl acetate | | 29.00 | 10.00 | 11.00 | | 13.00 | |
| 4-tert-Butyl-1-cyclohexanol | | | 20.00 | 22.00 | 25.00 | 25.00 | 20.00 |
| Clove absolute | | | | | | | |
| (−)-(1′R,E)-3,3-Dimethyl-5-(2′,2′,3′- | | | | | | | |

TABLE 1-continued trimethyl-3'-cyclopenten-1'-yl)-4-penten-2-ol [1]
Essential cedar oil
3,5,5-Trimethyl-1-hexanol                                5.00
Cardamome essential oil
Orange terpenes
Patchouli essential oil

[1] Origin: Firmenich SA, Geneva, Switzerland
[2] 3-(4-tert-butylphenyl)propanal; origin: Firmenich SA, Geneva, Switzerland
[3] 4-cyclohexyl-2-methyl-2-butanol; origin: Firmenich SA, Geneva, Switzerland
[4] 3-(4-tert-butylphenyl)-2-methylpropanal; origin: Givaudan SA, Vernier, Switzerland
[5] 8,12-epoxy-13,14,15,16-tetranorlabdane; origin: Firmenich SA, Geneva, Switzerland

TABLE 2

| MOC INGREDIENT | Ingredient Malodor Inhibition Value (%) Concentration in Medium (w/v %) | | | | | | | | MOC COMPOSITIONS 11 12 13 14 (Ingredient concentration w/w %) | | | |
|---|---|---|---|---|---|---|---|---|---|---|---|---|
|  | 0.0006 | 0.0012 | 0.0025 | 0.005 | 0.0125 | 0.025 | 0.05 | 0.1 | 11 | 12 | 13 | 14 |
| (E)-2-Dodecenal* |  | 10.37 | 29.72 | 55.42 | 86.93 | 94 |  |  |  |  |  |  |
| Mixture of tridecanal & 2-methyldodecanal* |  |  | 29.11 | 39.43 | 83.49 |  |  |  |  |  |  |  |
| 8-Isopropyl-6-methyl-bicyclo[2.2.2]oct-5-ene-2-carbaldehyde* |  |  | 18.91 | 28.29 | 76.89 | 84.45 | 82.89 | 88.20 |  |  |  | 25 |
| 3-(3-Isopropyl-1-phenyl)butanal* |  |  | 16.63 | 30.10 | 73.81 | 95.51 | 99.45 | 97.34 |  |  |  | 25 |
| (E)-2-Decenal |  |  | 21.97 | 28.18 | 66.63 | 90.11 | 100 |  |  |  |  | 25 |
| Mixture of 3-(4-methyl-3-pentenyl)-3-cyclohexene-1-carbaldehyde & 4-(4-methyl-3-pentenyl)-3-cyclohexene-1-carbaldehyde |  |  | 0.00 | 0.00 | 62.75 | 93.89 | 94.75 |  |  | 25 | 25 |  |
| 9-Undecenal* |  |  | 0.00 | 0.00 | 62.41 | 88.95 | 81.80 | 77.86 |  | 25 |  |  |
| Vetyver Haiti |  |  | 0.00 | 0.00 | 58.97 | 58.6 |  |  |  | 25 |  |  |
| Vetyverone |  |  | 10.9 | 10.40 | 44.6 |  | 47.1 | 54.2 |  |  |  | 25 |
| 4,5,6,7,8,9,10,11,12,13-Decahydrocyclododeca-1,3-oxazole |  |  | 0.00 | 0.00 | 52.20 |  |  |  |  |  |  | 25 |
| 2-Tridecenal (ethyl citrate solution) |  |  | 28.98 | 40.19 | 50 | 81 |  |  |  | 25 |  |  |
| 10-Undecenal |  |  | 3.00 |  | 49.2 |  |  |  | 20 | 25 |  |  |
| Mixture of 10-undecenal & 9-undecenal |  |  | 8.26 | 2.38 | 49.2 |  |  |  | 20 |  |  |  |
| Nonanal |  |  | 5.26 | 5.08 | 40.21 | 80.43 | 94.81 | 97.81 | 20 | 25 |  |  |
| Orris concrete |  |  | 4.22 | 14.17 | 39.45 |  |  |  |  |  |  |  |
| (+)-(4R)-1-P-Menthene-9-carbaldehyde* |  |  | 0.00 | 3.44 | 34.61 | 81.68 | 97.82 |  |  | 25 |  |  |
| (E)-4-Decenal |  |  | 21.97 | 28.18 | 66.63 | 90.11 | 100 |  |  |  |  |  |
| 3,7-Dimethyloctanal |  |  | 0.00 | 0.00 | 18.1 | 66.7 |  |  |  |  |  |  |
| Eucalyptus essential oil |  | 37.87 | 72.74 |  |  |  |  |  |  |  |  |  |
| Mixture of 3-(3,3-dimethyl-5-indanyl)propanal, & 3-(1,1-dimethyl-5-indanyl)propanal |  |  | 0.00 | 0.00 | 52 |  |  |  |  |  |  |  |
| (Z)-4-Dodecenal |  | 0.00 | 0.00 | 6.96 | 76.53 |  |  |  | 20 |  |  |  |
| 3-(6,6-Dimethyl-bicyclo[3.1.1]hept-2-en-2-yl)propanal |  |  | 0.00 | 4.58 | 82.87 | 96.73 | 100 | 96.35 | 20 |  |  |  |

*Origin: Firmenich SA, Geneva, Switzerland

TABLE 3

| MOC COMPOSITION | Composition Malodor inhibition coefficient (%) Concentration in Medium (v/v %) | | |
| --- | --- | --- | --- |
| | 0.025 | 0.0125 | 0.00625 |
| 1 | 100.0 | 86.7 | 31.9 |
| 2 | 87.7 | 92.0 | 52.5 |
| 3 | 89.3 | 81.3 | 44.2 |
| 4 | 84.6 | 81.4 | 48.1 |
| 5 | 64.3 | 57.2 | 18.9 |
| 6 | 76.7 | 71.8 | 48.1 |
| 7 | 67.7 | 70.5 | 39.6 |
| 8 | 64.3 | 73.2 | 48.0 |
| 9 | 78.4 | 66.4 | 43.3 |
| 10 | 70.8 | 85.2 | 45.4 |

TABLE 4

| MOC COMPOSITION | Composition Malodor inhibition coefficient (%) Concentration in Medium (v/v %) | | |
| --- | --- | --- | --- |
| | 0.025 | 0.0125 | 0.00625 |
| 11 | 96.97 | 48.56 | 0 |
| 12 | 83.39 | 37.42 | 6.95 |
| 13 | 91.64 | 68.50 | 9.15 |
| 14 | 92.34 | 68.81 | 19.6 |

Example 15

Preparation of Perfuming Compositions Comprising the Malodor Counteracting (MOC) Compositions and Their Use to Reduce Perception of Sweat Malodor Novel perfuming compositions according to the invention were prepared by adding to a reference perfume A of the woody, oriental, spicy type, which showed no malodor reduction capability when tested on its own according to the Protocol A. described in Example 1, a variety of MOC compositions according to the invention, in a number of concentrations.

As is apparent from FIG. 1, the addition of the MOC compositions to perfume A rendered the novel perfumes of the invention very efficient to counteract sweat malodor. FIGS. 1 a) to d) represent the % of malodor inhibition obtained according to Protocol A. of the MOC compositions of the invention, which comprised at least 80% by weight of MOC ingredients according to the invention, when used at varied concentrations in the medium together with perfume A.

In FIGS. 1 a) and b) the concentration of (perfume A+MOC composition) was kept constant at 0.025% v/v in the medium, the relative proportions of perfume A/MOC composition varying from 100:1 to 1:1.

In FIGS. 1 c) and d) the perfume A concentration was kept constant at a value of 0.025% v/v relative to the medium, and the concentration of MOC composition in the latter was varied so as to obtain the concentrations of MOC composition in the medium indicated in the X axis.

When used in the test medium at a concentration of at least 0.015% v/v, relative to the total volume of the test medium, the MOC compositions of the invention provided malodor inhibition coefficients representing a malodor reduction of at least 30%, relative to the activity of the fragrance on its own, and in many cases well above 50%. In the figures, the concentration of MOC composition in the testing medium is indicated on the X axis.

Example 16

Preparation of Perfuming Compositions Comprising the Malodor Counteracting (MOC) Compositions and Their Use to Reduce Perception of Sweat Malodor Novel perfuming compositions according to the invention were prepared by adding to a reference perfume B of the aromatic, citrus, woody type, which showed no malodor reduction capability when tested on its own according to the Protocol A. described in Example 1, a variety of MOC compositions according to the invention, in a number of concentrations.

As is apparent from FIG. 2, the addition of the MOC compositions to perfume B rendered the novel perfumes of the invention very efficient to counteract sweat malodor. FIGS. 2 a) to d) represent the % of malodor inhibition obtained according to Protocol A. of the MOC compositions of the invention, which comprised at least 80% by weight of MOC ingredients according to the invention, when used at varied concentrations in the fragrance.

When used in the test medium at a concentration of at least 0.004% v/v, relative to the total volume of the test medium, the MOC compositions of the invention provided malodor inhibition coefficients representing a malodor reduction of at least 30%, relative to the activity of the fragrance on its own, and in many cases well above 50%. In the figures, the concentration of MOC composition in the medium is indicated on the X axis. The perfume B was used in the test medium at a fixed concentration of 0.025% v/v, whereas the concentration of the MOC composition was varied as indicated in the graphs.

Example 17

Malodor Counteracting (MOC) Effect of Compositions and Their Use to Reduce Perception of Sweat Malodor In Vitro The MOC compositions of the invention were added, at a variety of concentrations, to a conventional spray body antiperspirant product representative of the silicone based antiperspirants, containing a silicone base sold under the tradename Dow Corning 245.

The novel body deodorants thus obtained were tested for their ability to mask or inhibit malodor generated in a medium containing bacterial cells of Staphylococcus haemolyticus, grown and incubated in a similar manner as previously described, and following the Protocol B. hereafter.

Protocol B. In-Vitro Malodor Inhibition as Evaluated by a Sensory Panel of Individuals.

This protocol follows the same principle as Protocol A. except that the detection system for measuring the malodor reduction capability of the compositions or products according to the invention is different. In the case of the present protocol the detection is sensorial, carried out by a panel of evaluators, on blind tests.

The Cys-Gly precursor, S-[1-(2-hydroxyethyl)-1-methylbutyl]-L-cysteinylglycine, used at 0.01 mM in the medium, is subject to bacterial transformation both in the absence (blank test) and in the presence of each MOC composition, perfuming composition or deodorant/antiperspirant product according to the invention, depending on which product's malodor reduction activity one wishes to evaluate.

The malodor generated by the bacterial transformation is evaluated olfactively (sensorial evaluation) on a defined scale of malodor intensity.

The bacterial cells of *Staphylococcus haemolyticus* are grown and incubated as previously described in Protocol A. 0.1 Volumes of the final bacterial suspension are added to each test sample (final volume 450 μl).

General Procedure: Test samples: reagents are admixed (product to be tested, precursor and bacterial cell suspension), and the reaction is started by adding the bacterial cell suspension as the last reagent, so as to form the testing medium; the samples are then incubated at 37° C. for 18-20 h. In parallel, two reference samples are prepared: a negative reference consisting of a 3 μg/ml solution of the Cys-Gly precursor in the 0.1 M potassium phosphate buffer at pH 7.5, which has no malodor (malodor intensity value zero), and a positive reference which contains the same amount of Cys-Gly precursor buffer solution, and the bacterial cells of *St. haemolyticus*, but contains no MOC composition or product according to the invention. These positive and negative references are incubated under the same conditions as the test samples, and provide the reference for the maximum malodor value in the scale of evaluation, normally 5 or close to 5.

Once the test samples and references are ready for evaluation, a panel of evaluators is asked to measure the malodor intensity of each of the samples, on a blind test and according to the following scale: 0=imperceptible malodor; 1=very weak malodor; 2=weak malodor; 3=moderate malodor; 4=intense malodor; 5=very intense malodor.

The responses from the various panelists are averaged and corrected statistically for standard deviation, to provide a value of malodor intensity for the test sample, and the two reference samples. The "malodor reduction value" for the test sample is then the difference between the positive reference malodor intensity value and the test sample malodor intensity value.

The antiperspirant samples were tested according to this Protocol B, at a defined volume concentration, relative to the total volume of medium, and the ability of the tested deodorant sample to cover the malodor of the evaluation medium was determined through sensorial evaluation by the panel.

In this manner, novel deodorant samples were prepared by adding MOC composition 9, in a variety of weight concentrations relative to the weight of deodorant spray, and were tested for their ability to cover the medium's malodor—the deodorant on its own, without the MOC composition of the invention, showed no malodor coverage ability (malodor reduction value=0) under the testing conditions indicated.

FIG. 3 shows the results of these tests—it is clear from this figure that the MOC composition 9 according to the invention is capable of reducing the sweat malodor when incorporated in the deodorant product, at concentrations varying from 0.05 to 2% weight, relative to the weight of deodorant. The malodor reduction values of the deodorants according to the invention reached values close to 4, at concentrations of MOC composition close to 1% w/w, relative to the weight of deodorant sample.

Examples 18-19

Malodor Counteracting (MOC) Effect of Compositions and Their Use to Reduce Perception of Human Sweat Malodor In Vitro Antiperspirant (AP) spray samples containing MOC composition 1 described in Example 1, as well as perfume A, were prepared using a variety of MOC composition concentrations, and 0.2% weight of the fragrance, relative to the deodorant weight, added to a conventional AP spray base prepared as described here below. The AP base on its own, and containing the perfuming compositions according to the invention, were then tested as described hereafter for their ability to reduce the malodor perceived.

The human sweat samples were incubated for 18-24 h with a mixture of bacterial strains commonly known to generate axillar malodor, and composed of *S. haemolyticus* and a mixture of *Corynebacterium xerosis* ATCC 373 and *Corynebacterium tuberculostearicum* strains. Sweat malodor samples were thus obtained and subsequently treated with the antiperspirant samples containing the MOC compositions of the invention, and evaluated on a blind test by a panel of individuals. The protocol used is described in detail by M. Troccaz et al. in Chemistry and Biodiversity, 2004, 1, 1022-1034.

Malodor intensity values were attributed via a sensory panel evaluation, on blind tests. The panel used a sensory intensity scale from 1 (no malodor) to 5 (very strong malodor) to assess the deodorant performance after 18 to 24 hours of incubation.

A reference control sample, containing only the mixture of sweat and bacteria cells, was evaluated at the same time, providing a rating for the maximum malodor intensity (5 or close to 5).

A typical antiperspirant spray base was used, comprising the ingredients listed here below on Table 5, in the proportions indicated, the mixture of which was formulated as an aerosol spray by using 25% weight of the AP base suspension and 75% weight of propellants, typically a mixture propane/butane at a pressure of 2.5 bar.

TABLE 5

| AP Spray Base Suspension | |
|---|---|
| Ingredient | Weight (%) |
| Dow Corning 345 Fluid[1] | 51.8 |
| Isopropyl Myristate | 8.75 |
| Silica | 1 |
| Quaternium-18 Hectorite[2] | 3.25 |
| Aluminium Chlorohydrate | 32 |
| Perfume | 3.2 |

Figure 4:
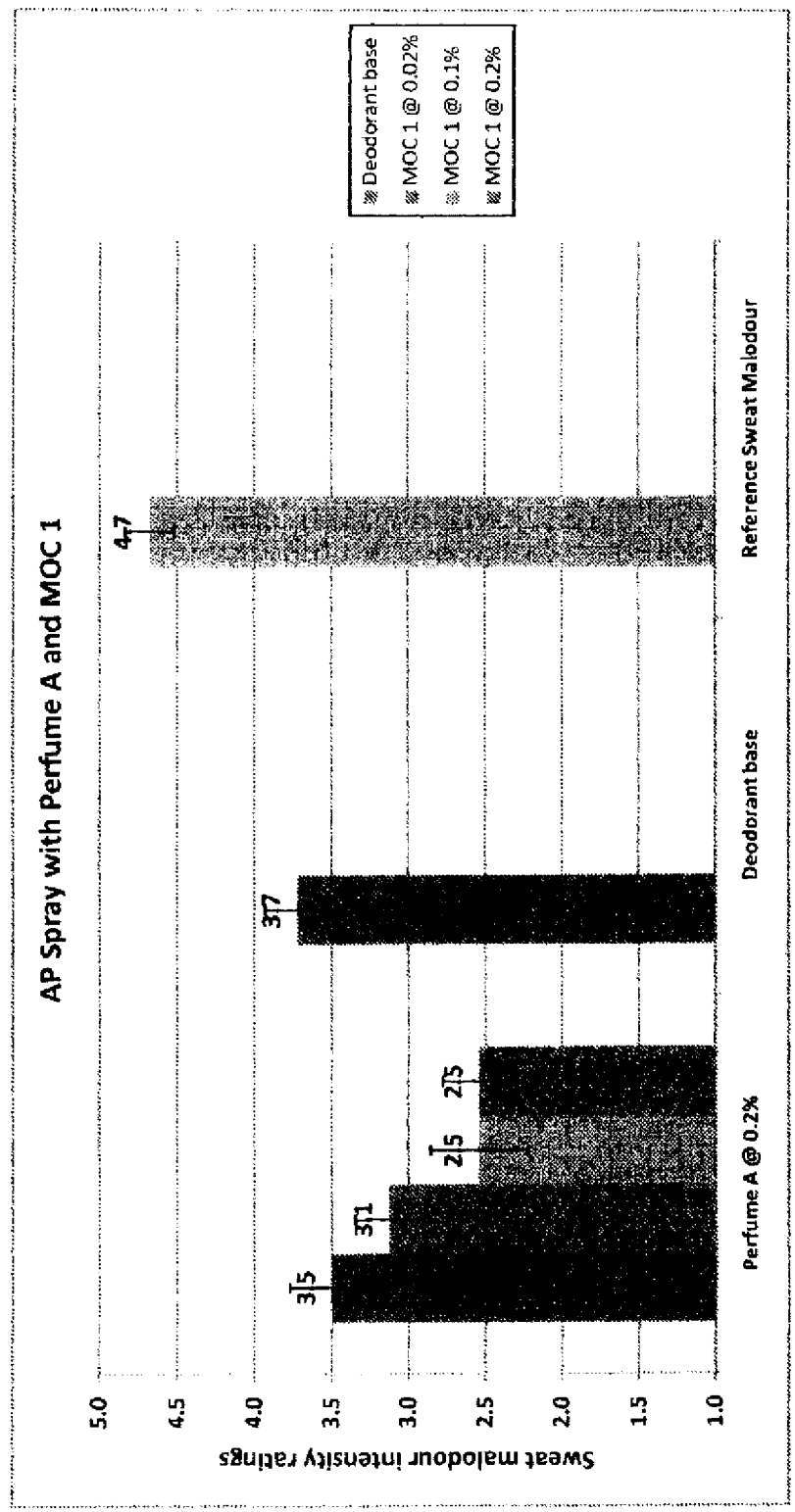
FIG. 4 shows the malodor counteraction effectiveness of an antiperspirant product comprising MOC composition 1, and the mixture of the latter with Perfume A, as measured via the panel sensory method described in Example 18.

[1]Cyclopentasiloxane (and) Cyclohexasiloxane; origin: Dow Corning.
[2]Suspending agent; origin: RHEOX The results of the evaluation tests are shown in FIG. 4, wherein the MOC composition 1 according to the invention is designated simply as MOC 1. It is quite clear from this graph that the deodorant products comprising the MOC and perfuming compositions of the invention can reduce the malodor perception by above 2 units on the scale of 1 to 5 and that the MOC composition 1 of the invention effectively increases the deodorant base's activity, and that of the combination of deodorant base plus Perfume A, masking ability by at least one such unit, when used at appropriate concentrations in the deodorant product.

According to another embodiment, antiperspirant (AP) samples, containing MOC composition 9 described in Example 9, were prepared by using the suspension base described above (without propellant) and a variety of MOC composition concentrations, relative to the deodorant suspension weight. The results of the testing are shown in FIG. 7, which clearly shows that MOC composition 9 significantly reduces the malodor intensity perceived by the panel, even when present at low concentrations in the AP spray suspension base. The latter appears to have no significant malodor reduction capability on its own, whereas when comprising the MOC composition 9 (simply designated as MOC 9 in the graph) it shows a malodor reduction value of up to 2, at MOC 9 weight concentrations of 1% w/w, relative to the weight of the AP base.

Examples 20-21

Figure 5:
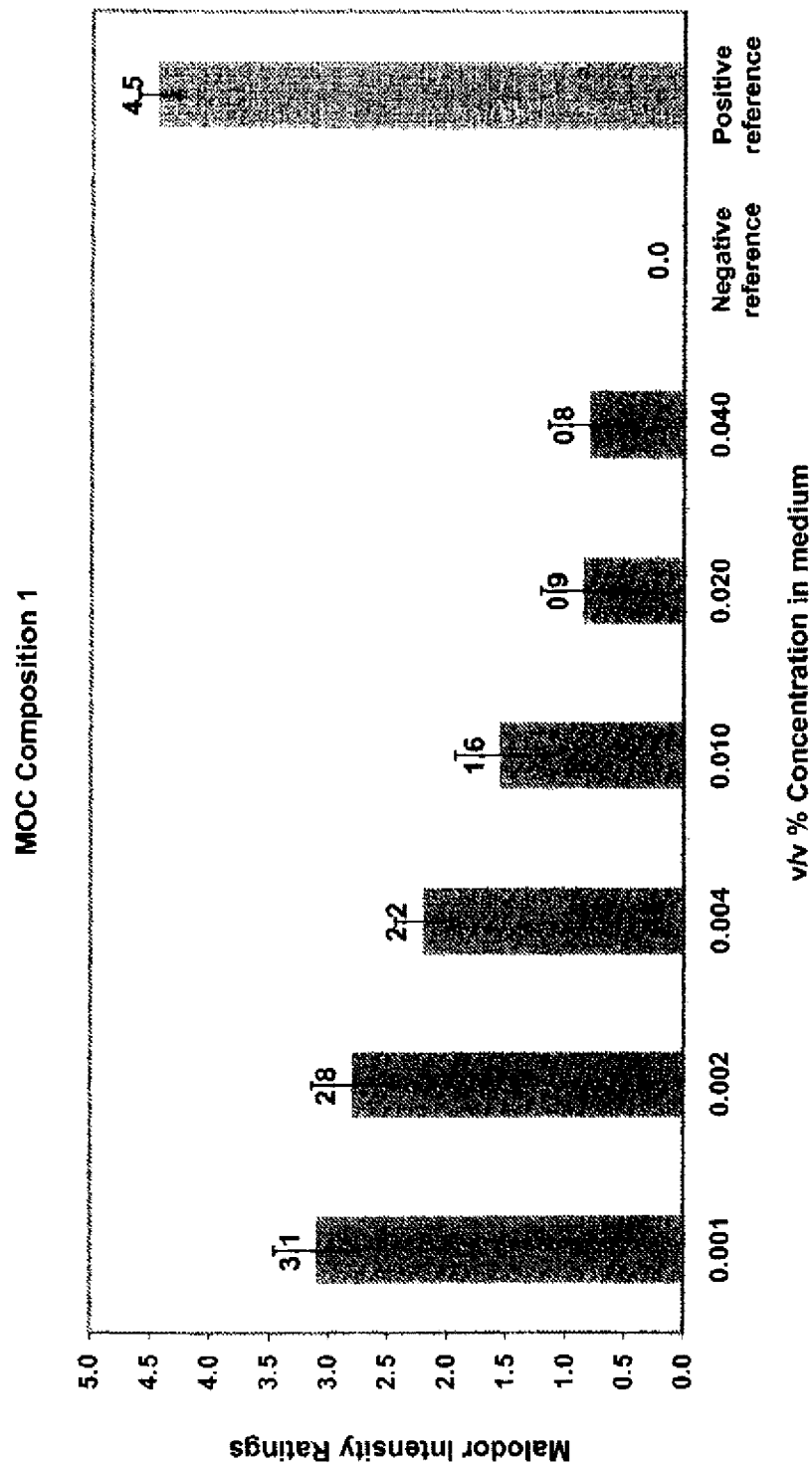
FIG. 5 shows the malodor counteraction effectiveness of MOC composition 1, at various volume % concentrations in the testing medium, as measured via the panel sensory method described in Example 17.

Malodor Counteracting (MOC) Effect of Compositions and Their Use to Reduce Perception of Sweat Malodor In Vitro MOC composition 1 of the invention was evaluated, according to Protocol B. described in Example 17, for its ability to reduce malodor perceived from the medium, when present in the latter in a variety of concentrations. FIG. 5 shows the results of the panel evaluations. It is clear from this graph that composition 1 is capable of reducing the malodor perceived by the panel, relative to a maximum malodor reference, by a value (malodor reduction value) of about 1.5 to as much as almost 4, depending on its volume concentration in the medium.

Similar tests were carried out, using the same Protocol B. described in Example 17, with MOC composition 9 and the results are shown in FIG. 6, again showing great efficacy of the latter to reduce the malodor perceived by the panel, particularly at concentrations of 0.004% v/v and above, relative to the volume of the medium.

Example 22

Malodor Counteracting (MOC) Effect of Composition 1 to Reduce Perception of Sweat Malodor In Vivo, in the Form of a Spray Deodorant According to the Invention A standard deodorant test to measure the efficacy of a deodorant spray containing 0.4% by weight of MOC Composition 1 described in Example 1 was carried out. The deodorant spray composition is described here below. The objective was to demonstrate 5 hour and 24 hour efficacy of the MOC composition.

Alcoholic deodorant spray composition (30% solution/70% Propane-Butane 2.5 bar) for in vivo assay, ingredients and respective concentrations:

| | |
|---|---|
| Ethanol 95° | 86.67% |
| Glyceryl ricinoleate | 1% |
| Caprylic/capric triglyceride | 11% |
| MOC Composition 1 | 1.33% |

A team of three trained panelists between the ages of 20 and 40 years was selected for olfactory evaluation, each of them being able to detect the reduction of body odour, following the application of a deodorant product, on a 0 (no odor) to 5 (very strong odor) linear scale.

A panel of 31 male subjects aged within the range of from 20 to 50 years were denied the use of any type of deodorant or antiperspirant during two weeks before the start of the test, and were assigned a non-deodorant, unperfumed, soap bar for exclusive use of bathing.

On the first day of the test, the body odor of each of the panelists' axillae was assessed by the trained assessors and assigned a score corresponding to the strength of the odor on the scale of 0 to 5. Then the axillae were washed by a technician according to a standardized method, using an unperfumed soap bar, wiped with a water rinsed flannel, and dried with a clean towel.

The deodorants were applied by the technician in a standard application according to an experimental design, whereby each product was applied to the same number of left and right axillae. The panelists then left the test centre.

On the same day there was an additional assessment 5 hours after application to test for 5 hour efficacy. There was no further application of product at this stage.

On the second day panelists attended at the same time, i.e. 24 hours later. The intensity of their body odor was evaluated by all three assessors, they sniffed each axilla and scored for body odor as before. Then the axillae were washed and a second application of product was made.

The assessment and application were repeated on the third and fourth days, and on the fifth day a final assessment was performed.

The body odor scores were averaged and are shown in the Table hereafter.

TABLE

Mean malodor scores after application as described above

| Time after application | Score |
|---|---|
| Just after | 1.99 |
| 5 Hours | 0.97 |
| Day 1 | 1.33 |
| Day 2 | 1.33 |
| Day 3 | 1.08 |
| Day 4 | 0.80 |

After 5 and 24 hours following application of the product according to the invention, there were reductions in mean malodor, significant at the 99.99% confidence level. This showed conclusively that MOC composition 1 gave 24 hour protection against body odor. After continued application for the rest of the week, mean malodor scores continued to fall, suggesting a build-up in efficacy. After 4 days application the reduction in malodor was in the region of about 60% relative to the value immediately after application. The reduction in malodour is about 50% 5 hours after application.

The results above show that the composition according to the invention significantly reduces sweat malodour for more than 24 hours after application, when applied in vivo in the form of a spray deodorant product.

What is claimed is:

1. A composition comprising:
   a 9,12-octadecadienoic acid;
   a 9,12,15-octadecatrienoic acid; and
   3-(4-tert-butylphenyl)propanal; and
   wherein the total concentration of the 9,12-octadecadienoic acid and the 9,12,15-octadecatrienoic acid is at least 50% by weight of the composition; and
   wherein the concentration of 3-(4-tert-butylphenyl)propanal is 5-30% by weight of the composition.

2. A deodorant composition comprising:
   a 9,12-octadecadienoic acid;
   a 9,12,15-octadecatrienoic acid; and
   3-(4-tert-butylphenyl)propanal; and
   wherein the weight ratio of the sum of the 9,12-octadecadienoic acid and the 9,12,15-octadecatrienoic acid to the 3-(4-tert-butylphenyl)propanal is 50:30 to 95:5; and
   wherein the total concentration of the 9,12-octadecadienoic acid, the 9,12,15-octadecatrienoic acid, and the 3-(4-tert-butylphenyl)propanal is 0.3 to 10% by weight of the deodorant composition.

3. An antiperspirant composition comprising:
a 9,12-octadecadienoic acid;
a 9,12,15-octadecatrienoic acid; and
3-(4-tert-butylphenyl)propanal; and
wherein the weight ratio of the sum of the 9,12-octadecadienoic acid and the 9,12,15-octadecatrienoic acid to the 3-(4-tert-butylphenyl)propanal is 50:30 to 95:5; and
wherein the total concentration of the 9,12-octadecadienoic acid, the 9,12,15-octadecatrienoic acid, and the 3-(4-tert-butylphenyl)propanal is 0.3 to 10% by weight of the antiperspirant composition.

4. A body care product comprising at least 0.5% by weight, relative to the total weight of the product, of the composition of claim 1.

5. The body care product of claim 4 wherein the composition is present in an amount of 1 to 5% by weight, relative to the total weight of the product.

6. A body deodorant product comprising at least 0.5% by weight, relative to the total weight of the product, of the composition of claim 1.

7. The body deodorant product of claim 6 wherein the composition is present in an amount of 1 to 5% by weight, relative to the total weight of the product.

8. An antiperspirant product comprising at least 0.5% by weight, relative to the total weight of the product, of the composition of claim 1.

9. The antiperspirant product of claim 8 wherein the composition is present in an amount of 1 to 5% by weight, relative to the total weight of the product.

10. The composition of claim 1, further comprising a perfuming co-ingredient.

11. A perfume, body spray, or cologne comprising the composition of claim 10.

12. A method of counteracting sweat malodor, the method comprising applying to a sweat-generating skin surface the composition of claim 1 or a body-care product comprising at least 0.5% by weight of the composition of claim 1, wherein the body-care product is selected from the group consisting of a perfume, a deodorant, and an antiperspirant.

* * * * *

UNITED STATES PATENT AND TRADEMARK OFFICE
CERTIFICATE OF CORRECTION

PATENT NO. : 9,101,783 B2
APPLICATION NO. : 13/319411
DATED : August 11, 2015
INVENTOR(S) : Troccaz et al.

Page 1 of 23

It is certified that error appears in the above-identified patent and that said Letters Patent is hereby corrected as shown below:

Please delete Patent 9101783 in its entirety and insert Patent 9101783 in its entirety as shown on the attached pages Signed and Sealed this
Eighth Day of March, 2016

Michelle K. Lee
*Director of the United States Patent and Trademark Office*

(12) United States Patent
Troccaz et al.

(10) Patent No.: US 9,101,783 B2
(45) Date of Patent: Aug. 11, 2015

(54) MALODOR COUNTERACTING COMPOSITIONS AND METHOD FOR THEIR USE TO COUNTERACT SWEAT MALODOR

(75) Inventors: Myriam Troccaz, Saint-Julien-en-Genevois (FR); Sabine Beccucci, Etaux (FR); Monica Bandera, Perroy (CH); Manuel Bourgaux, Echenevex (FR); Catherine Selig, Geneva (CH); Magali Latenlere, Geneva (CH); Anthony Clark, Manhattan, NY (US)

(73) Assignee: Firmenich SA, Geneva (CH)

( * ) Notice: Subject to any disclaimer, the term of this patent is extended or adjusted under 35 U.S.C. 154(b) by 239 days.

(21) Appl. No.: 13/319,411

(22) PCT Filed: Jun. 17, 2010

(86) PCT No.: PCT/IB2010/052736

§ 371 (c)(1),
(2), (4) Date: Nov. 8, 2011

(87) PCT Pub. No.: WO2010/146556

PCT Pub. Date: Dec. 23, 2010

(65) Prior Publication Data

US 2012/0052031 A1 Mar. 1, 2012

(30) Foreign Application Priority Data

Jun. 19, 2009 (WO) ............... PCT/IB2009/052634

(51) Int. Cl.
| | |
|---|---|
| A61Q 15/00 | (2006.01) |
| A61K 8/33 | (2006.01) |
| A61K 8/34 | (2006.01) |
| A61K 8/35 | (2006.01) |
| A61K 8/36 | (2006.01) |
| A61K 8/37 | (2006.01) |
| A61K 8/49 | (2006.01) |

(52) U.S. Cl.
CPC . *A61Q 15/00* (2013.01); *A61K 8/33* (2013.01); *A61K 8/34* (2013.01); *A61K 8/342* (2013.01); *A61K 8/35* (2013.01); *A61K 8/361* (2013.01); *A61K 8/37* (2013.01); *A61K 8/4973* (2013.01); *A61K 2800/77* (2013.01)

(58) Field of Classification Search
CPC ...... A61K 8/33; A61K 8/361; A61K 31/201; A61K 31/202
See application file for complete search history.

(56) References Cited

U.S. PATENT DOCUMENTS

| | | | |
|---|---|---|---|
| 2,976,321 A * | 3/1961 | Dorsky et al. | 568/425 |
| 5,213,791 A | 5/1993 | Lyon et al. | 424/65 |
| 5,487,886 A | 1/1996 | Lyon et al. | 424/65 |
| 5,595,728 A | 1/1997 | Brockett et al. | 424/65 |
| 5,649,979 A | 7/1997 | Paget et al. | 8/137 |
| 5,994,291 A | 11/1999 | Aida et al. | 512/8 |
| 6,060,043 A | 5/2000 | Hayden et al. | 424/65 |
| 6,133,228 A | 10/2000 | Pika et al. | 512/21 |
| 6,218,355 B1 | 4/2001 | Herrmann | 512/27 |
| 6,369,026 B1 | 4/2002 | Pika et al. | 512/21 |
| 6,677,297 B2 | 1/2004 | Frerot | 512/20 |
| 7,723,286 B2 | 5/2010 | Fehr et al. | 512/8 |
| 7,935,669 B2 | 5/2011 | Fehr et al. | 512/1 |
| 2002/0037264 A1 | 3/2002 | Burry et al. | 424/65 |
| 2004/0102357 A1 | 5/2004 | Smith et al. | 512/3 |
| 2005/0223940 A1 | 10/2005 | Perring et al. | 512/1 |
| 2006/0228250 A1 * | 10/2006 | Brown et al. | 422/5 |
| 2007/0298994 A1 | 12/2007 | Finke et al. | 512/1 |
| 2008/0025935 A1 | 1/2008 | Starkenmann et al. | 424/65 |
| 2010/0098650 A1 | 4/2010 | Herrmann et al. | 424/65 |
| 2011/0288165 A1 * | 11/2011 | Bruheim et al. | 514/458 |

FOREIGN PATENT DOCUMENTS

| | | |
|---|---|---|
| DE | 30 03 494 A1 | 8/1980 |
| EP | 0 829 463 A2 | 3/1998 |
| EP | 0 936 211 B1 | 8/1999 |
| EP | 0 971 021 A1 | 1/2000 |
| GB | 2 041 964 A | 9/1980 |
| WO | WO 95/04809 A1 | 2/1995 |
| WO | WO 95/08976 A1 | 4/1995 |
| WO | WO 98/47477 A1 | 10/1998 |
| WO | WO 99/60990 A2 | 12/1999 |
| WO | WO 01/28980 A1 | 4/2001 |
| WO | WO 03/049666 A2 | 6/2003 |
| WO | WO 2004/009051 A2 | 1/2004 |
| WO | WO 2004009051 A2 * | 1/2004 |
| WO | WO 2005/044206 A1 | 5/2005 |
| WO | WO 2006/079934 A2 | 8/2006 |
| WO | WO 2008/093272 A2 | 8/2008 |

OTHER PUBLICATIONS

CAS Registry No. 80-54-6 (Nov. 16, 1984).*
CAS Registry No. 18127-01-0 (Nov. 16, 1984).*
International Application No. PCT/IB2010/052736, Partial International Search Report dated Nov. 22, 2011.
Troccaz et al., "3-Methyl-3-sulfanylhexan-l-ol as a Major Descriptor for the Human Axilla-Sweat Odour Profile," Chemistry & Biodiversity, 1:1022-1035 (2004).
Troccaz et al., "Properties of Recombinant *Staphylococcus haemolyticus* Cystathionine β-Lyase (metC) and Its Potential Role in the Generation of Volatile Thiols in Axillary Malodor," Chemistry & Biodiversity, 5:2372-2385 (2008).

* cited by examiner

Primary Examiner — Bethany Barham
Assistant Examiner — Peter Anthopolos
(74) Attorney, Agent, or Firm — Winston & Strawn LLP

(57) ABSTRACT

The invention relates to a malodor counteractancy or counteracting (MOC) method that resorts to the use of specific malodor counteracting (MOC) mixtures of MOC ingredients. More particularly, the invention relates to new MOC compositions capable of neutralizing or masking in an efficient manner sweat malodor and which can be used in perfumes, deodorants, antiperspirants and other body care products.

12 Claims, 9 Drawing Sheets

FIGURE 1
a)
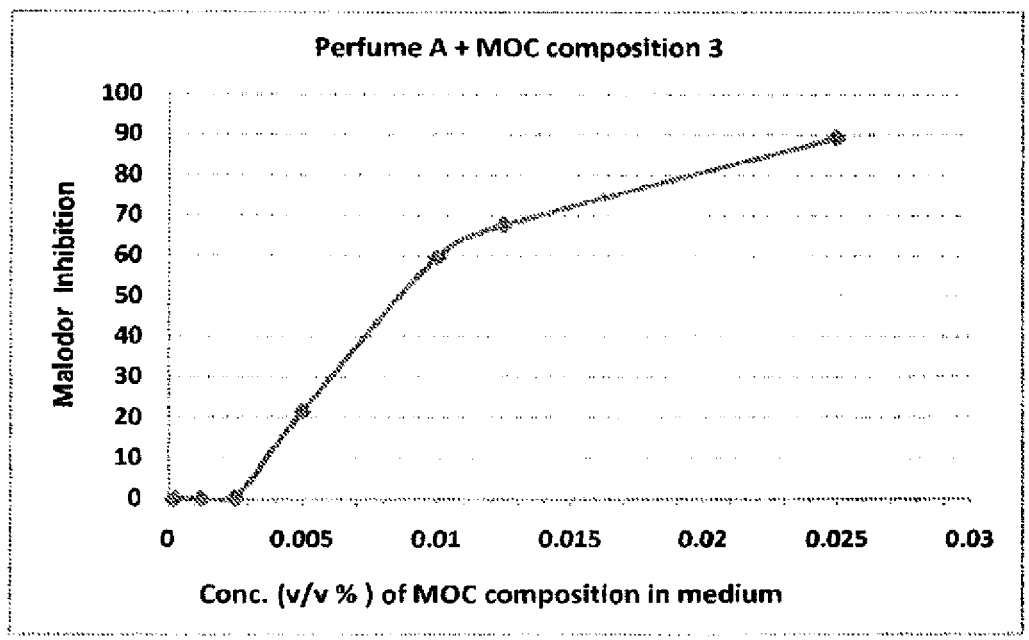
b)
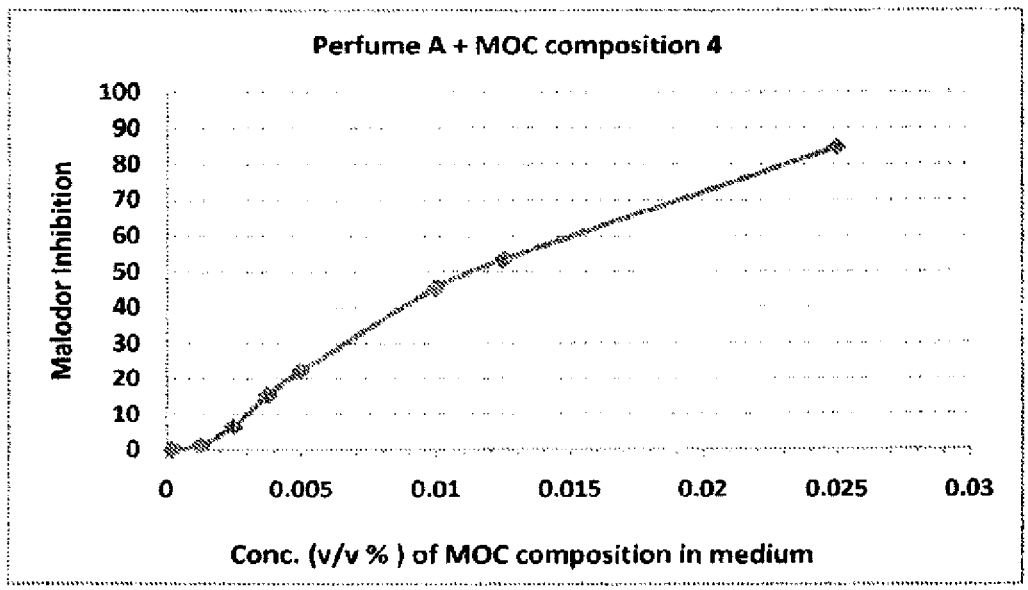

FIGURE 1 (continued)
c)
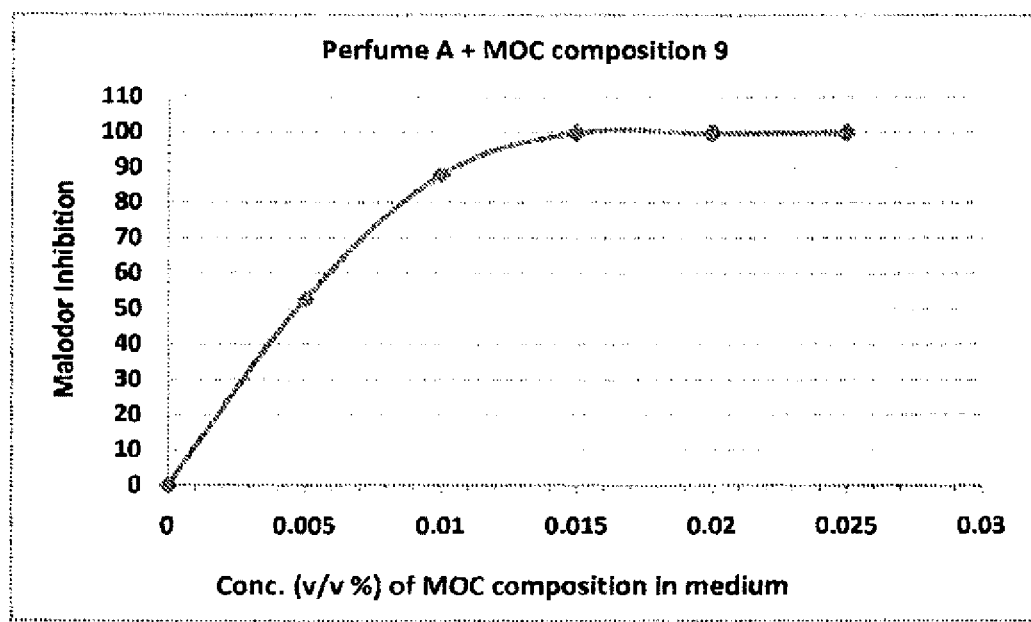
d)
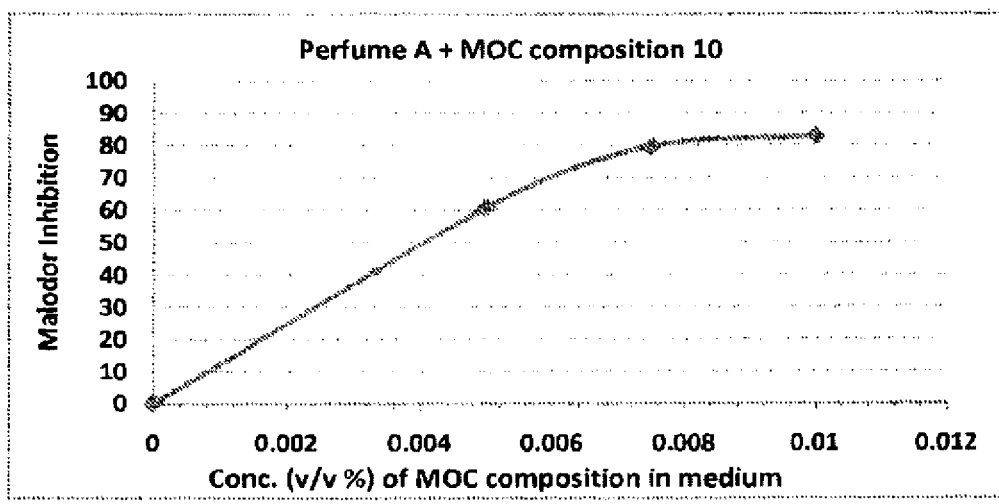

FIGURE 2
a)
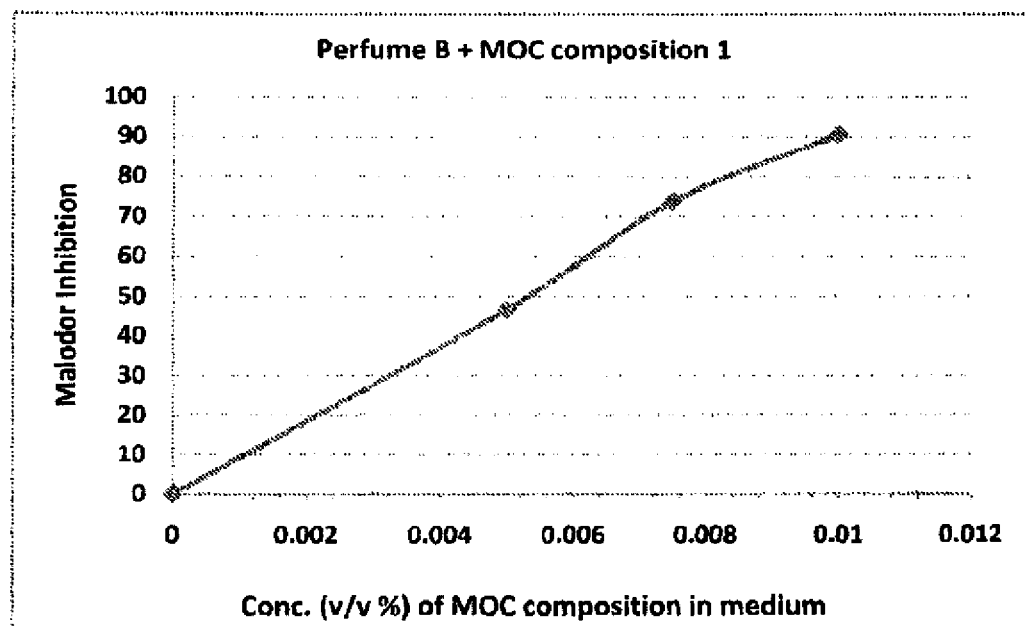
b)
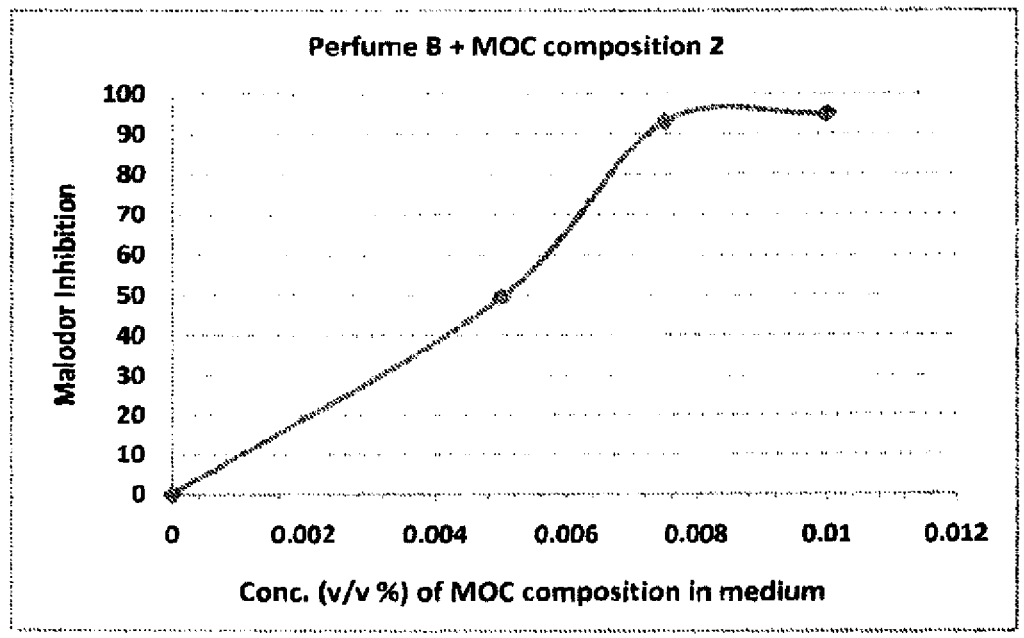

FIGURE 2 (continued)
c)
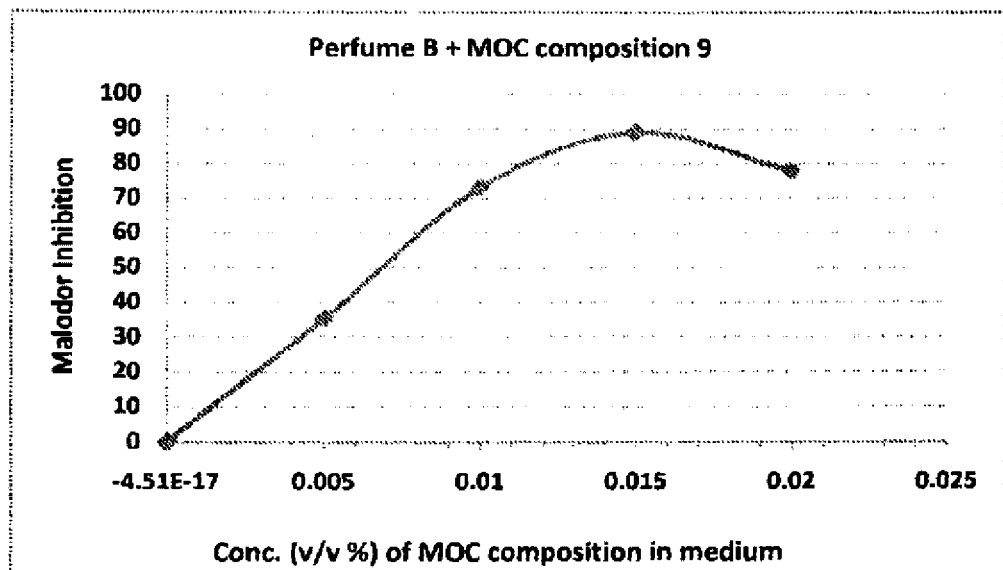
d)
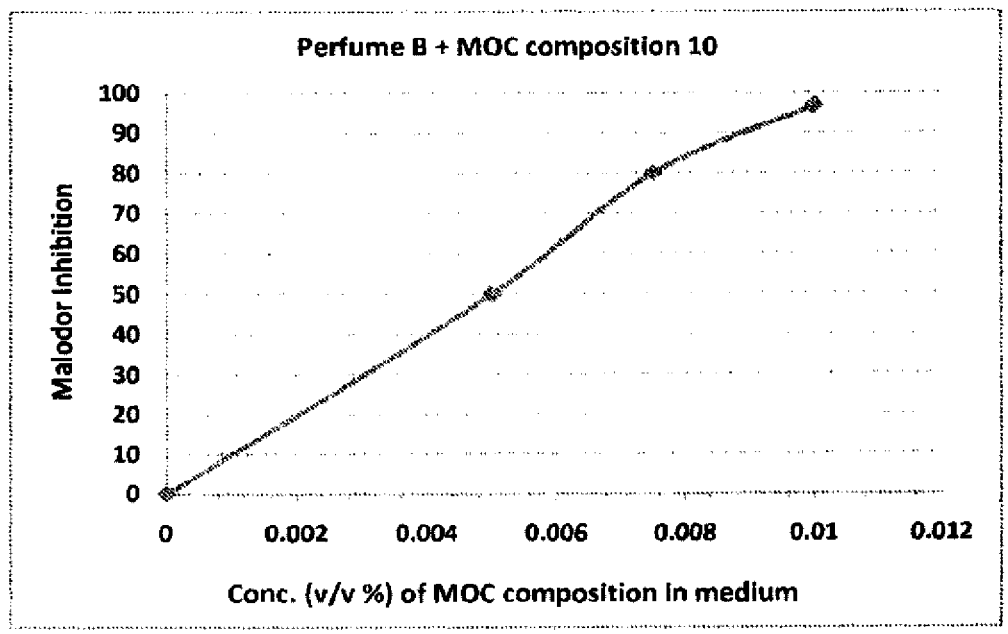

FIGURE 7

AP Spray suspension Base with MOC 9

MALODOR COUNTERACTING COMPOSITIONS AND METHOD FOR THEIR USE TO COUNTERACT SWEAT MALODOR

This application is a 371 filing of International Patent Application PCT/IB2010/052736 filed Jun. 17, 2010.

TECHNICAL FIELD

The present invention relates to a malodor counteracting (MOC) method that resorts to the use of specific malodor counteracting (MOC) mixtures of MOC ingredients, which act as deodorant or deodorizing compositions. More particularly, the invention relates to new deodorant or MOC compositions and consumer products containing them, namely perfumes, colognes, body sprays, deodorants and antiperspirants, capable of efficiently neutralizing or masking sweat malodor. The novel MOC compositions of the invention contain at least one effective MOC ingredient and are characterized by a malodor inhibition coefficient of at least 50%, at a defined composition concentration in an appropriate medium, against malodor generated by *Staphylococcus haemolyticus* enzymatic activity in said medium, together with a malodor reduction value of at least 2, relative to a maximum malodor score value of 5, measured under the same conditions but in the absence of the MOC composition.

The invention also relates to methods of use of the MOC compositions and of any finished consumer products containing them.

PRIOR ART

The prior art's richness in reports of methods to counteract and/or mask malodors, and more particularly sweat malodor, is such that a complete review of all the methods and compositions prior reported in this context is impossible here. It is clear however that there still exists a need to continue searching alternative ways of solving the sweat malodor problem, as evidenced by the constant publication of new methods of solving malodor occurrence.

In the field of sweat malodor counteraction, methods which resort to the use of compositions or products free from, or having a reduced content in, classical deodorant or antiperspirant ingredients, in particular aluminum or zirconium salts, well-known for their deodorant activity, are especially appreciated. The present invention aims at bringing a novel contribution in this context, by providing novel deodorant and antiperspirant compositions capable of counteracting, and more preferably suppressing, sweat malodor, whilst reducing or eliminating content in any such classical ingredients, and whilst also providing an efficient sensorial coverage of the malodor perceived by the user of such deodorant or antiperspirant products and/or of any other individuals present in the proximity of that user.

Although the prior art has previously reported a large variety of methods to identify ingredients and consumer products able to inhibit or reduce the occurrence of sweat malodor by interfering with the activity of axillary microorganisms responsible for generating such malodor, we have now surprisingly established that many such methods do not provide a full solution to the problem of inhibiting or suppressing sweat malodor.

For example, U.S. Pat. No. 5,213,791 discloses deodorant consumer products containing effective amounts of inhibitors of an amino acid β-lyase enzyme which contains the co-factor pyridoxal phosphate and catalyzes human body malodor, wherein the inhibitor is hydroxylamine or an aminoacid of formula $H_2N-O-CH(R)COOH$, R being hydrogen or a defined radical. Amongst the aminoacids of the latter formula, aminooxyacetic acid is preferred. Other documents in the same family, i.e. U.S. Pat. Nos. 5,595,728 and 5,487,886, further disclose inhibitors of specific formulae, as defined in the above documents. These prior art documents assume that sweat malodor is essentially generated by aminoacid β-lyase enzymes containing the pyridoxal phosphate co-factor and do not teach or suggest anything about inhibition of malodor resulting from the activity of enzymes which do not contain this co-factor and which generate sweat malodor through the cleavage of different precursors than those taught in these documents.

In a more recent document, U.S. Pat. No. 6,060,043, the malodor counteracting efficacy of some of the amino-acid derivatives taught in the above mentioned patent family have been put into doubt, and a novel solution based on the use of amino acids strictly in the D-form has been proposed.

Other efforts to attempt to provide valid solutions to the sweat malodor problem have relied on the increasing knowledge available on the nature of the chemical species thought to be responsible for the perception of sweat malodor and propose the use of specific chemicals as malodor standards to identify possible modulators of the malodor. One can cite in this context the contribution disclosed in US 2007/0298994, which relies on the use of 3-mercapto-3-methyl-hexan-1-ol as malodor standard. This compound had been reported a few years before as an important component of human sweat, and already proposed as a possible representative of the sulfury notes typical of sweat malodor, capable of serving as a malodor marker, but its use as a sensory marker as taught in the above-mentioned US application has not provided heretofore a quantitative solution to sweat malodor counteraction, very likely because the latter problem is more complex and cannot be solved through the sensory coverage of this compound's odor alone.

The present applicant has also provided a prior art contribution in WO 2006/079934, wherein there is described a method for screening compounds capable of inhibiting the malodor generated by the enzymatic activity of a variety of microorganisms, when the latter are put into contact with specific precursors as taught therein. A large amount of possible precursors is disclosed in this document, which also suggests a very large group of possible malodor inhibiting compounds, based on the structure of the precursors used, but gives no guidance as to the use of other malodor modulators, not structurally related to the precursor.

The present invention aims at providing a new and quantitative solution to the problem of sweat malodor reduction and more preferably suppression and inhibition thereof, by providing methods for the creation and use of specific and efficient malodor counteracting (MOC) compositions and products, which rely on specific combinations of ingredients presenting well-defined malodor counteracting parameters that we have surprisingly established as being essential to ensure efficient sweat malodor suppression. The present invention therefore provides an original and advantageous contribution to the solution of the sweat malodor problem.

SUMMARY AND DESCRIPTION OF THE INVENTION

The present invention relates to malodor counteracting (MOC) compositions able to at least reduce, and more preferably suppress, sweat malodor, comprising at least 30% by weight, relative to the weight of MOC composition, of at least one MOC ingredient, wherein the latter is characterized by a malodor inhibition coefficient of at least 25%, at a MOC ingredient weight per volume (w/v) concentration in an appropriate medium, against malodor generated by *Staphylococcus haemolyticus* enzymatic activity in said medium.

We have now surprisingly established that compositions containing such an ingredient or ingredients are capable of efficiently suppressing sweat malodor.

The parameters defining the MOC ingredients according to the invention are a result of the fact that we have surprisingly established that certain ingredients could effectively interfere with the bacterial activity on fresh sweat, so as to modify this activity in a manner making it possible to reduce or suppress the formation of malodor. Fresh sweat does not have a bad odor, but upon activity thereon of bacteria present on the skin, in particular on the axillary skin, certain precursors contained in the sweat generate malodorant metabolites. The MOC ingredients according to the invention, having a malodor inhibition coefficient of at least 25%, at a concentration of ingredient in the appropriate medium of at least 0.005% w/v, relative to the total volume of the medium, effectively interfere with such bacterial activity which is typically of an enzymatic nature, presenting a capacity to reduce or entirely suppress sweat malodor.

Compositions comprising one or more ingredients, and preferably at least three MOC ingredients, as defined above, are preferred according to the invention. Even better performing MOC compositions according to the invention are those which comprise one or more ingredients characterized by a malodor inhibition coefficient of at least 30%, and preferably of 50% or more, at an ingredient concentration, in the appropriate medium, of at least 0.0125% w/v, relative to the volume of the medium.

As used herein, "a malodor counteracting (MOC) composition" is to be understood as a mixture of one or more MOC ingredients as defined above and which is capable of at least reducing the perception of malodor, i.e. of an odor that is unpleasant or offensive to the human nose.

According to the invention, the individual MOC ingredients, and their mixtures and compositions containing such MOC ingredients, as defined herein, can be used to reduce the malodor perceived from sweat, either as collected from individuals and used in a medium or surface which is not part of the human body, or in the form of sweat present on a sweated surface such as skin, hair or clothing, and as perceived by an individual or individuals in the vicinity of the malodor source.

By "a malodor inhibition coefficient" it is understood here a % inhibition value, relative to reference conditions, which is measured via a method essentially similar to that generally described in WO 2006/079934, more particularly on pages 8 and 11-15 of the above document, and in the examples thereprovided, and which requires that an ingredient to be screened be put into contact with bacterial cells of *Staphylococcus haemolyticus*, or with a β-lyase present in such cells, in the presence of a specific precursor of malodorant metabolites. The reference conditions correspond to 0% of malodor inhibition, i.e. to 100% generation of the malodorant metabolites under the screening conditions, in the absence of the MOC ingredient or composition.

The type of *Staphylococcus haemolyticus* strain suitable for use according to the invention is any one of the common strains of this bacterium which colonizes the human underarm region and has been found to efficiently release volatile sulfur compounds when put into contact with sweat or with a sulphur precursor typically present in fresh sweat. Useful such strains have been previously cited in WO 2006/079934, and many others can be used in the measurements according to the invention. The typical and preferred conditions of preparation of these bacteria strains are described in detail in this prior art document, and in the examples presented further on, wherein the specific *Staphylococcus haemolyticus* CNCM I-4170 strain has been used in the appropriate medium providing definition of the characterizing malodor inhibition coefficient for the ingredients and compositions according to the invention.

Further details of such a screening and % inhibition measurement and definition are described further on in this application. The precursor used, which may also be in the form of a human sweat sample, typically generates malodorant sulfur compounds when acted upon by the *Staphylococcus haemolyticus* cells, or by a β-lyase present in such cells. The malodor inhibition coefficient, as defined herein, reflects the % of reduction in free SH groups generated in the abovementioned medium by the enzymatic activity of the bacterial cells when in presence of the MOC ingredient or MOC composition in question, as compared to the same measurement in their absence.

The concentration in free SH groups can be detected via commonly known methods, as described in WO 2006/079934, and in a more recent disclosure by M. Troccaz et al. in Chemistry and Diversity, 2008, vol. 5, pages 2372 to 2385, more particularly page 2384. A malodor inhibition coefficient of 30% for example, therefore means a capacity of the MOC ingredient to reduce by 30% the concentration of SH groups in the appropriate medium, as compared to the concentration thereof in the absence of said ingredient.

By an "appropriate medium" we mean here the medium wherein the appropriate precursor, and more preferably the Cys-Gly precursor exemplified further on, is put into contact with bacterial cells of *Staphylococcus haemolyticus*, under the generally known conditions described in WO 2006/079934, and to which the MOC ingredient or composition, as the case may be, is added to counteract the malodor generated by the bacterial or enzymatic cleavage of the precursor.

More specifically, by the "appropriate medium", in which the MOC ingredient presents the defined malodor inhibition coefficient, it is understood here a medium consisting essentially of a suspension of bacterial cells of *Staphylococcus haemolyticus* in a buffer, preferably 100 millimolar potassium phosphate (pH 7.5) buffer, also comprising a sulphur precursor of sweat malodor, preferably the Cys-Gly precursor S-[1-(2-hydroxyethyl)-1-methylbutyl]-L-cysteinylglycine, at a weight concentration of 0.17 millimolar (mM). Alternatively, the bacterial cells can be replaced by a β-lyase present in said cells.

The defined concentration of the MOC ingredient in the appropriate medium is understood here to mean a weight % concentration of at least 0.005%, relative to the volume of said medium (w/v %). More preferably, this concentration shall be at least 0.0125% w/v. Even more preferably, the MOC ingredient shall be present in the medium at a concentration of between 0.0125 and 0.05% or even 0.1% w/v, to provide a malodor inhibition coefficient of at least 30%, and more preferably above 50%, relative to the maximum malodor reference under the same conditions.

According to the invention, the MOC compositions may contain 50% by weight or more, relative to the weight of composition, of MOC ingredients.

According to preferred embodiments of the invention, the MOC compositions comprise at least 30% by weight of said MOC ingredient or ingredients, each of which is characterized by a malodor inhibition coefficient of at least 50% at a minimal concentration of 0.0125 w/v and more preferably 0.025%. The more active and preferred MOC ingredients for the MOC compositions of the invention shall be characterized by a malodor inhibition coefficient of 75% or more, at a concentration in the medium of at least 0.0125 or 0.0250 w/v. relative to the volume of the medium.

A second parameter possibly characterizing the MOC ingredients and compositions according to the invention, is a "malodor reduction value", which is understood here to be a value reflecting the perceived malodor reduction obtained in the presence of said MOC ingredient or composition, as compared to a reference value defined under similar conditions but in the absence of said ingredient or composition. The defined value is the result of a panel sensorial test and is defined on a scale of measurement wherein the reference value of maximum malodor perception (no malodor reduction at all) corresponds to 5.

It is therefore the difference between the maximum malodor perceived by a panel of evaluator individuals from the bacterial transformation of either sweat collected from human axilla, or of an appropriate precursor typically present in sweat, and the malodor perceived by the same evaluating panel from the same bacterial transformation, under similar conditions, but when the latter is carried out in the presence of the MOC ingredient or composition. Both the defined and the reference values are averaged values, statistically treated for standard deviation. A malodor reduction value of 2 for example means therefore that the malodor score attributed by the panel, on average, when the MOC ingredient or composition is applied to the sweat/bacteria containing sensory evaluation medium (or to the precursor/bacteria containing sensory evaluation medium), under controlled conditions, is reduced by 2 units relative to the reference value of the maximum sweat malodor perceived from the same medium, under the same conditions, when no MOC ingredient or composition is added thereto.

The sensory panel methods used for defining this malodor reduction value are described further on in the examples. They provide a sensory measure of the capacity of said ingredient or composition to effectively reduce the malodor perceived by the evaluators upon application of the compositions of the invention to sweated or sweat-containing media or surfaces.

By contrast, the malodor inhibition coefficient is an analytically determined value of the same capacity to reduce sweat malodor, but measured as a function of the concentration, in the appropriate medium, of metabolites resulting from the bacterial transformation of an appropriate precursor capable of generating said malodorant metabolites in the presence of *Staphylococcus haemolyticus*. We have now been able to establish that the MOC compositions of the invention which have a combination of these two parameters as described below provide unexpected efficacy against sweat malodor.

The MOC compositions according to the invention, which more preferably comprise at least three MOC ingredients as defined above, possess surprisingly useful malodor counteracting properties against sweat malodor and they are capable of masking, reducing, or even suppressing and/or neutralizing the latter, when applied to sweat collected from the axilla of individuals or to precursors present in such sweat. Moreover, they render consumer products such as perfumes, colognes and body sprays, or yet body deodorants and antiperspirants, to which they are added, particularly effective against malodor generated by body sweat.

MOC compositions wherein each of said MOC ingredients are characterized by a malodor inhibition coefficient of at least 50%, at an ingredient concentration of at least 0.0125% w/v in the appropriate medium and, amongst these, compositions comprising MOC ingredients characterized by at least 75% malodor inhibition coefficient are surprisingly advantageous and provide above 80% malodor reduction.

The malodor counteracting (MOC) compositions of the invention thus obtained are characterized by a malodor inhibition coefficient of about 40% or more, at a MOC composition volume/volume (v/v) concentration in the appropriate medium of at least 0.0125%. against malodor generated by *Staphylococcus haemolyticus* enzymatic activity in said medium. The malodor reduction value of such compositions is typically of at least 2, on the sensory scale wherein the maximum malodor reduction value, measured in the absence of the MOC composition, is 5. Moreover, amongst the latter, the MOC compositions of the invention which are characterized by a malodor inhibition coefficient of at least 50% against sweat malodor generated by the activity of a mixture of bacteria of *Staphylococcus haemolyticus* and a mixture of *Corynebacterium* spp. on human skin, or on sweat collected from human skin, preferably from the axillary area, provide advantageous consumer products against sweat malodor.

By a defined "MOC composition concentration" it is understood here a volume/volume concentration of at least 0.01%, relative to the volume of the sensory evaluation medium, defined as previously. More preferably, this concentration shall be at least 0.0125% v/v and preferably it will be comprised between 0.0125 and 0.05, or even 0.1% v/v, relative to the volume of the medium.

Preferred MOC compositions of the invention are also compositions wherein the MOC ingredients or ingredients are selected from the group consisting of: (−)-(2E)-2-ethyl-4-[(1R)-2,2,3-trimethyl-3-cyclopenten-1-yl]-2-buten-1-ol; 3-(4-tert-butylphenyl)propanal; 4-cyclohexyl-2-methyl-2-butanol; 3-(4-tert-butylphenyl)-2-methylpropanal; (+)-(1S,2S,3S)-2,6,6-trimethyl-bicyclo[3.1.1]heptane-3-spiro-2'-cyclohexen-4'-one; cashmeran (1,2,3,5,6,7-hexahydro-1,1,2,3,3-pentamethyl-4-indenone); 9,12-octadecadienoic acid, 9,12,15-octadecatrienoic acid, and mixtures thereof; nerolidol; 1,4-dioxacyclohexadecane-5,16-dione; 8,12-epoxy-13,14,15,16-tetranorlabdane; (−)-(1'R,E)-3,3-dimethyl-5-(2',2',3'-trimethyl-3'-cyclopenten-1'-yl)-4-penten-2-ol; (E)-2-dodecenal; 3-decanal, 2-methyldecanal and mixtures thereof; 8-isopropyl-6-methyl-bicyclo[2.2.2]oct-5-ene-2-carbaldehyde; 3-(3-isopropyl-1-phenyl)butanal; (E)-2-decenal; 3-(4-methyl-3-pentenyl)-3-cyclohexene-1-carbaldehyde, 4-(4-methyl-3-pentenyl)-3-cyclohexene-1-carbaldehyde and mixtures thereof; 9-undecenal; vetyver essential oil; vetyverone; 4,5,6,7,8,9,10,11,12,13-decahydrocyclododeca-1,3-oxazole; 2-tridecenal; 9-undecenal, 10-undecenal and mixtures thereof; nonanal; (+)-(4R)-1-p-menthene-9-carbaldehyde; (E)-4-decenal; 3,7-dimethyloctanal; eucalyptus essential oil; 3-(3,3-dimethyl-5-indanyl)propanal, 3-(1,1-dimethyl-5-indanyl)propanal and mixtures thereof; (Z)-4-dodecenal; 3-(6,6-dimethyl-bicyclo[3.1.1]hept-2-en-2-yl) propane; and mixtures of two or more of the preceding ingredients.

Sweat malodor counteracting compositions comprising at least 30% by weight, relative to the total weight of the composition, of ingredients selected from the group above-defined are preferred.

Amongst the latter, embodiments of the compositions in which at least 50% by weight of the MOC composition is formed of 9,12-octadecadienoic acid, 9,12,15-octadecatrienoic acid, or mixtures thereof, provide excellent malodor counteracting products, particularly when they further comprise from 5 to 30% by weight of 3-(4-tert-butylphenyl)propanal.

Typically, any particular embodiments of the MOC compositions of the invention, characterized by at least 60% malodor inhibition coefficient, at a composition concentration of at least 0.0125% v/v in the appropriate medium, against malodor generated by *Staphylococcus haemolyticus* enzymatic activity in said medium, and a malodor reduction value of at least 2, and preferably 3 or 4, provide prime embodiments of the MOC compositions.

All the MOC compositions of the invention, in particular embodiments, may be essentially or entirely formed, i.e. contain more than 50% by weight, or be formed essentially of 100% by weight of MOC ingredients, the latter being defined as previously anywhere in this description. This means therefore that the MOC compositions may "consist" (contain 100% by weight of) said MOC ingredients.

Specific examples of embodiments of MOC compositions according to the invention are presented further on.

The MOC compositions of the invention are particularly useful for the preparation of consumer products capable of reducing or suppressing the body malodor generated by sweating, to which they are added in a generally known manner and in concentrations which are dependent of the MOC activity of said composition and of the nature of the consumer product into which the latter is incorporated. The invention therefore also relates to such consumer products, of which perfumes, colognes and body sprays are particular examples, as they are typically used by the consumer to provide a pleasant scent to skin and hair in particular. Of course, such perfuming compositions may also be used to spray textiles for example, in particular clothes and other body and hair wear textiles, which can acquire malodor through the user's sweating, so as to possibly prevent the development of malodor from textiles carrying fresh sweat and small amounts of skin bacteria.

As "perfuming compositions" according to the invention it is understood here compositions which are distinct from the MOC compositions previously defined (formed of only MOC ingredients). The perfuming compositions typically contain the MOC composition together with a perfuming co-ingredient, a solvent or an adjuvant or carrier of current use in perfumery, or a mixture of two or more of the latter.

The MOC composition may be used in the perfuming compositions in a large variety of concentrations, comprised between 10 and 80% by weight of the weight of perfuming composition, and more preferably of at least 20% by weight of the latter's total weight.

Preferred embodiments of the perfuming compositions of the invention, namely perfumes, colognes, body sprays, may comprise from 40 to 60% by weight of MOC composition as defined previously.

A perfuming composition which has a malodor inhibition coefficient of at least 60%, measured at a defined perfuming composition concentration in the appropriate medium, against malodor generated by *Staphylococcus haemolyticus* enzymatic activity in said medium, and a malodor reduction value of at least 3, is also an object of the present invention.

By a defined "perfuming composition concentration" it is understood here a concentration of at least 0.02% v/v, and more preferably comprised between 0.025 and 0.05% v/v, relative to the volume of the medium.

To provide the desired MOC effects to counteract sweat malodor, a MOC ingredient can be used on its own, more preferably in the form of the above-defined MOC compositions, or yet in the form of the perfuming compositions containing in particular perfuming co-ingredients, meaning other ingredients added mainly for their perfuming effect. Therefore, the perfuming compositions of the invention comprise at least two distinct components, the MOC composition of the invention and a mixture of fragrance ingredients typically of a different nature and which are essentially intended to provide a desired hedonic effect of a pleasant nature.

By a "perfuming co-ingredient" it is meant here a compound of current use in perfumery, which is used in perfuming a composition or consumer product, to impart a pleasant odor thereto. In other words, such a co-ingredient must be recognized by a person skilled in the art as being able to impart or modify, in a positive or pleasant way, the odor of a composition, and not just as having an odor.

The nature and type of the perfuming co-ingredients of the MOC composition in the perfumes and perfuming compositions of the invention do not warrant a more detailed description here, which in any case would not be exhaustive, the skilled person being able to select them on the basis of its general knowledge and according to intended use or application and the desired perfuming effect. In general terms, these perfuming co-ingredients belong to chemical classes as varied as alcohols, aldehydes, ketones, esters, ethers, acetates, nitriles, terpene hydrocarbons, nitrogenous or sulfurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, and in other works and textbooks of a similar nature, as well as in the abundant patent literature in the field of perfumery. It is also understood that said co-ingredients may also be compounds known to release in a controlled manner various types of perfuming compounds, either through chemical reaction cleavage of chemical bonds of heavier precursors or through physical release of such perfuming compounds, for example when the latter are encapsulated or carried in emulsion, microemulsion and/or nanoemulsion type perfume carrier system.

As liquid carriers for such perfuming ingredients or as components of the perfuming compositions of the invention, one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as di-propylene glycol, diethyl phthalate, isopropyl myristate, benzyl benzoate, 2-(2-ethoxyethoxy)-1-ethanol or ethyl citrate, which are commonly used. Others, having an equivalent function of solubilizing the MOC compositions and their perfuming co-ingredients, are equally adapted to be used in the perfuming compositions of the invention.

The perfuming co-ingredients, as well as the MOC ingredients and compositions of the invention, used to prepare the perfuming compositions, and consumer products such as body deodorants and antiperspirants, may also be present in a solid form, encapsulated or dispersed in solid carriers. As appropriate solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- and Geliermittel in Lebensmittel, Band 2 der Schriftenreihe Lebensmittelchemie, Lebensmittelqualität, Behr's Verlag-GmbH & Co., Hamburg, 1996 and other textbooks in the art of encapsulation or entrapment of compounds and compositions such as perfumes, flavors and pharmaceuticals.

Encapsulation is a well known process to a person skilled in the art, and may be performed, for instance, using techniques such as spray-drying, agglomeration or yet extrusion; or it may also consist of a coating encapsulation method, including coacervation and complex coacervation techniques, core shell encapsulation methods, etc. Provided that the encapsulation system does not negatively affect the MOC activity and efficacy of the MOC compositions, or of the perfuming compositions of the invention, any type of delayed release system carrier, providing for physical release of the entrapped materials, is adapted as a carrier for the MOC and perfuming ingredients and compositions as defined herein.

Preferred encapsulates of the MOC ingredients and compositions of the invention, and of the perfuming co-ingredients, which can be used in the perfuming compositions and other consumer products cited above, are the microcapsule systems commercialized by Firmenich SA (Switzerland) under the tradenames Fircaps® and PopScent® for example, based respectively on modified starch and melamine resin or polyurea type carriers.

The MOC and perfuming ingredients may also be used in the form of chemical release systems, i.e. heavier molecules which are capable of releasing the MOC ingredient and/or perfuming ingredient by chemical cleavage under the conditions of use—many such chemical release systems have been disclosed in the prior art, namely in the patent literature, which release the MOC ingredient via hydrolysis, photolysis or other such reaction mechanisms. One may cite in this context prior art documents such as for example WO 95/04809, EP 0971021, WO 03/049666, EP 0936211, WO 99/60990, WO 01/28980, WO 08/093272, WO 98/47477, US 2004/0102357, DE 3003494 and WO 95/08976, provided that such chemical release systems, under the conditions of their application, allow the release of the corresponding active MOC ingredient.

It goes without saying that, provided the encapsulation or chemical release technologies for delayed release of an ingredient or composition in application, does not interfere with the capacity of said ingredient or composition to fulfill the objective of the present invention, i.e. the reduction or suppression of sweat malodor, particularly in axillar skin, any combination thereof with the present invention malodor counteraction technology is appropriate to provide composition embodiments of the invention as presently disclosed and claimed.

As mentioned above, consumer products containing the MOC compositions or the perfuming compositions of the invention, such as body deodorants and antiperspirants, are also an object of the present invention. The nature of such products can be any and is well-known to the person skilled in the art of cosmetics and products for body and hair care in particular. These consumer products are commonly perfumed and the MOC compositions of the invention can be added thereto as such, or as components of the perfuming compositions of the invention.

Such consumer products typically comprise a consumer product base, in addition to the MOC and/or perfuming composition of the invention.

For the sake of clarity, by "consumer product base" we mean here a base which is distinct from, but compatible with, the MOC and perfuming compositions of the invention, and which is typically formed of substances capable of achieving the functional effect required typically from that product, such as freshening, deodorizing and odor neutralizing. Typical consumer product bases are the functional mixtures of ingredients that form the base of for example a body care preparation such as a body deodorant or antiperspirant. The latter may assume any form that is current, such as for example the form of a cream, gel, spray, pump-spray or aerosol, or yet stick. Such deodorants and antiperspirants are very well-known to the cosmetic specialist and the choice of their ingredients and forms does not require any particular effort beyond the general skill of the practitioner in the art of cosmetics and particularly body deodorants and antiperspirants.

Thus the nature and type of the constituents of the consumer product base do not warrant a more detailed description here, which in any case would not be exhaustive, the skilled person being able to select them on the basis of its general knowledge and according to the nature and the desired effect of said product. Merely as examples of appropriate such bases, representative of deodorant and antiperspirant consumer products, one can cite in this context prior art documents such as U.S. Pat. No. 6,060,043 and US 2002/037264. The latter describe in detail the types of ingredients, and their concentration and function, which are common in such consumer product bases. Of course, many other prior art documents can be found which detail appropriate deodorant and antiperspirant bases in particular, into which the MOC compositions and perfuming compositions of the invention can be incorporated to provide a sweat malodor counteraction effect.

Some of the above-mentioned consumer product bases may represent aggressive media for the MOC or perfuming compositions of the invention, so that it may be necessary to protect the latter from premature decomposition, for example by encapsulation as previously mentioned.

The proportions in which the MOC compositions, or the perfuming compositions containing them, can be incorporated into the various aforementioned consumer products may vary within a wide range of values. These values are dependent on the nature of the product as well as on the desired malodor counteracting effect that one wants to achieve. In many of these consumer products, the amount of perfuming composition containing the MOC component that is typically added to the consumer product is comprised between 0.01 and 10%, more preferably of at least 0.5%, and even more preferably between 1 and 5%, by weight, of MOC or perfuming composition according to the invention, relative to the total weight of the consumer product. More common ranges are comprised between 0.05 and 5% by weight, or yet from 0.1 to 3% and more preferably between 0.3 and 2% by weight, relative to the weight of the deodorant or antiperspirant in which the compositions are incorporated.

A body deodorant or antiperspirant which has a malodor inhibition coefficient of at least 60%, measured at a concentration of at least 0.5% v/v of said deodorant or antiperspirant in the appropriate medium, against malodor generated by *Staphylococcus haemolyticus* enzymatic activity in said medium, and a malodor reduction value of at least 3, and more preferably 4, is also an embodiment of the invention.

According to another embodiment of the invention, there is provided a method to counteract sweat malodor, wherein there is applied to sweat, to a sweat-generating surface, or to a sweat-carrying surface, a malodor counteracting (MOC) composition as previously defined, in a form and amount appropriate and sufficient to reduce, mask, eliminate or prevent any sweat malodor perception by an individual exposed to the sweat or to said surface. Preferably, the MOC composition is applied to human skin or hair, and preferably to the human axillary skin. Any embodiment of the MOC composition, perfuming composition, or perfumed product previously described in this disclosure, is appropriate for use according to this method.

Embodiments of the method of the invention comprise methods wherein the MOC composition or perfuming composition of the invention is applied in the form of a perfuming composition, namely a perfume, a cologne, or in the form of a body deodorant or antiperspirant.

BRIEF DESCRIPTION OF THE DRAWINGS

FIGS. 1 a) to d) show the % malodor inhibition effectiveness of a reference Perfume A to which the MOC compositions of the invention described in Examples 1 to 10 were added in a variety of concentrations, as a function of the perfume's capability to reduce the malodor of sulfur-like smelling compounds generated according to the testing Protocol A. (Example 15).

FIGS. 2 a) to d) show the % malodor inhibition effectiveness of a reference Perfume B to which the MOC compositions of the invention described in Examples 1 to 10 were added in a variety of concentrations, as a function of the perfume's capability to reduce the malodor of sulfur-like smelling compounds generated according to the testing Protocol A. (Example 16).

FIG. 3 shows the malodor counteraction effectiveness of a spray deodorant product comprising MOC composition 9 of the invention, as measured via the panel based sensory method described in Example 17 as Protocol B.

FIG. 4 shows the malodor counteraction effectiveness of an antiperspirant product comprising MOC composition 1, and the mixture of the latter with Perfume A, as measured via the panel sensory method described in Example 18.

FIG. 5 shows the malodor counteraction effectiveness of MOC composition 1, at various volume % concentrations in the testing medium, as measured via the panel sensory method described in Example 17.

Figure 6:
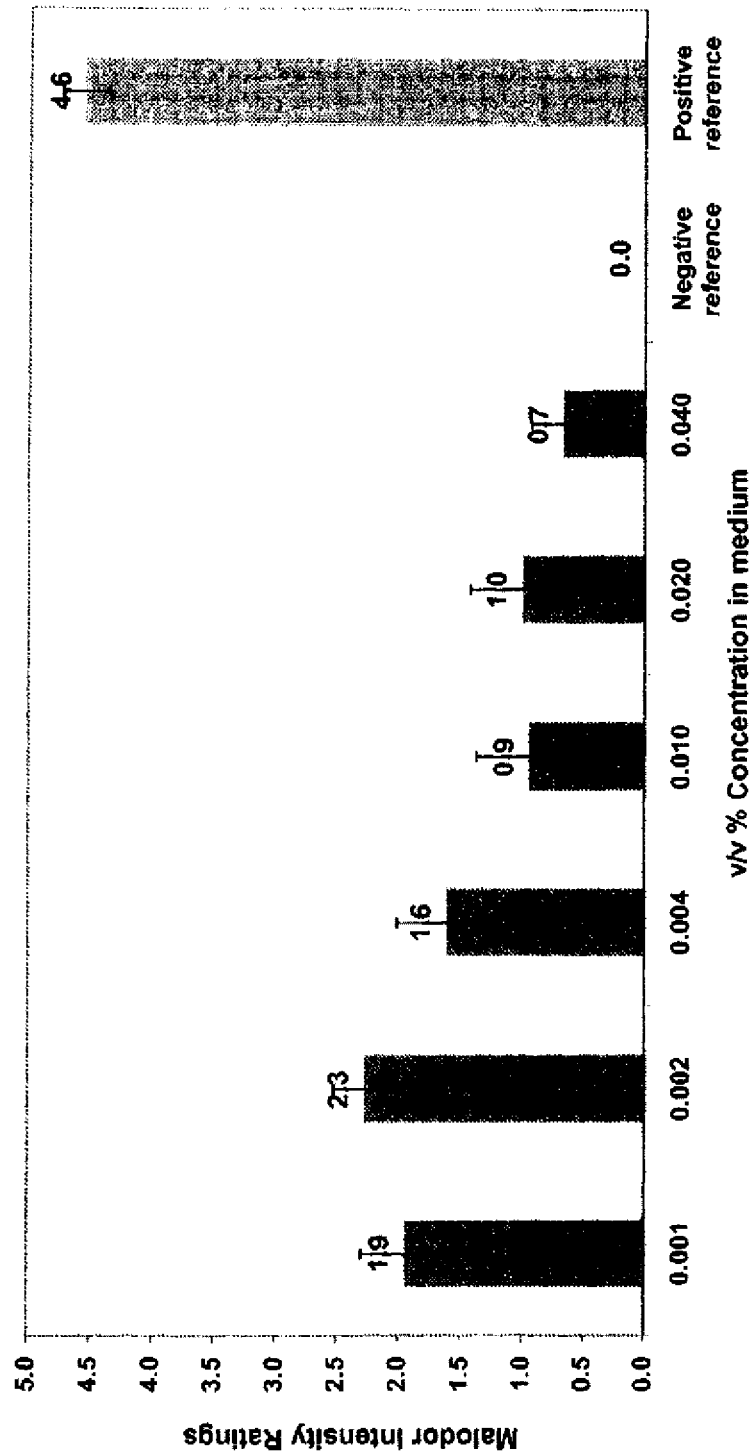
FIG. 6 shows the malodor counteraction effectiveness of MOC composition 9, at various volume % concentrations in the testing medium, as measured via the panel sensory method described in Example 17.

FIG. 6 shows the malodor counteraction effectiveness of MOC composition 9, at various volume % concentrations in the testing medium, as measured via the panel sensory method described in Example 17.

FIG. 7 shows the malodor counteraction effectiveness of MOC composition 9, at various weight % concentrations in the AP base described in Example 18, as measured via the panel sensory method described in Example 17.

EXAMPLES

The invention will now be described in further detail by way of the following examples.

Examples 1 to 14

Malodor Counteracting (MOC) Compositions and Their Use to Reduce Perception of Sweat Malodor A number of malodor counteracting compositions according to the invention were prepared by admixture, in the proportions indicated, of the MOC ingredients listed in Tables 1 and 2. The latter also summarize the ability of each of said ingredients to reduce sweat malodor, as evidenced by the respective malodor inhibition coefficient indicated for each ingredient. These values were measured via the method indicated hereafter, designated as Protocol A.

Protocol A. In-Vitro Malodor Inhibition of Individual MOC Ingredients—General Conditions of Evaluation A Cys-Gly precursor, S-[1-(2-hydroxyethyl)-1-methylbutyl]-L-cysteinylglycine, is subject to enzymatic transformation both in the absence (blank test) and in the presence of each MOC ingredient. Detection of enzymatic activity inhibition is measured via the sulfur groups, namely thiol groups, freed from the precursor bacterial transformation, by comparison with the reference experiment in the absence of the respective MOC ingredient, said sulfur groups being detected by interaction with DTNB, a known chemical detector system for thiols. The reaction can be monitored by absorbance reading at 412 nm. The procedure can be performed indifferently with either a purified or semi-purified enzyme or intact bacterial cells, as in the case described here. Malodor inhibition coefficient is measured as a function of the percentage of free thiol groups in the medium, over time, by an absorbance method, and reflects the reduction in malodor obtained in the presence of the MOC ingredients and compositions.

Reagents and Equipment

Preparation of Bacterial Suspension

*Staphylococcus haemolyticus* CNCM I-4170 was grown under generally known conditions in Brain-Heart Infusion plus 0.5% of Tween® 80. At the end of the growth phase, the bacterial cells were harvested by centrifugation at 5000 rpm for 15 min. The cell pellet was then washed with 0.1 volumes of sterile potassium phosphate buffer 0.1 M, pH 7.5. Cell pellets were finally concentrated 5 times in the same buffer. 0.25 Volumes of this suspension were then added to each sample to be tested, to a final volume of 200 µL.

Preparation of the Cys-Gly Precursor (Enzyme Substrate)

Cys-Gly-precursor (MM=292.1 g/mole), prepared as described in WO 2006/079934, was dissolved at 0.25 mg/ml in potassium phosphate buffer 0.1 M, pH=7.5, leading to a 0.86 mM solution. The precursor was used at 0.17 mM final concentration.

Detection Reagent DTNB

DTNB (5,5'-Dithio-bis-(2-nitrobenzoic acid; MM=396.36 g/mol) was prepared at 3.9 mg/ml (equivalent to 10 mM) in potassium phosphate buffer 50 mM, pH=7.5+0.1 mM EDTA. The reagent was used at 0.5 mM final concentration.

Reader Type:
Standard absorbance reader.

Liquid Handling:
Manual or automatic handling using a conventional robotic station.

General Procedure: reagents are admixed, and the reaction is started by adding the bacterial cell suspension as the last reagent.

Absorbance measurements, over time and relative to a blank, were taken, the final volume of each sample having been kept constant at 200 ml.

As is apparent from the Tables 1 and 2, the MOC ingredients according to the invention were active against sweat malodor in a range of concentrations varying from about 0.001 to 0.1% w/v, relative to the volume of the appropriate medium. Preferred activities were observed in a range of concentrations between 0.005 and 0.1% w/v.

Following this same procedure indicated above, but using instead of the individual ingredients the fourteen MOC compositions according to the invention listed in Tables 1 and 2, we established that each such composition was capable of providing the malodor reduction effect indicated in the results summarized in Tables 3 and 4.

As the results in Tables 3 and 4 show, the MOC compositions of the invention, which comprised at least 40% by weight, and in many cases 80% or more, of MOC ingredients according to the invention, when used at a concentration of at least 0.01% v/v relative to the total volume of the test medium, provided malodor inhibition coefficients representing a malodor reduction of at least 50%, relative to the activity of the reference, and even at lower concentrations were still able to provide an efficient malodor counteracting effect.

The compositions of the invention effectively reduced sweat malodor when used in a range of concentrations of between 0.006 and 0.025% v/v, relative to the appropriate medium volume, and had essentially suppressed all malodor at this higher range limit value of concentration.

TABLE 1

| MOC INGREDIENT | Ingredient Malodor Inhibition Value (%) Concentration in Medium (w/v %) | | | | | | | | MOC COMPOSITIONS 1 2 3 (Ingredient concentration w/w %) | | |
|---|---|---|---|---|---|---|---|---|---|---|---|
| | 0.0006 | 0.0012 | 0.0025 | 0.005 | 0.0125 | 0.025 | 0.05 | 0.1 | | | |
| (−)-(2E)-2-Ethyl-4-[(1R)-2,2,3-trimethyl-3-cyclopenten-1-yl]-2-buten-1-ol [1] | | 0.00 | 21.16 | 70.79 | 79.96 | 80.33 | | | 6.00 | | |
| Bourgeonal [2] | | 4.15 | 7.06 | 42.61 | | | | | 2.70 | | |
| Coranol ® [3] | | 0.00 | 0.00 | 10.83 | 49.78 | 77.73 | | 77.76 | | | |
| Lilial ® [4] | | 0.90 | 9.47 | 37.51 | 80.98 | 89.99 | | | 7.70 | 3.50 | 58.00 |
| (+)-(1S,2S,3S)-2,6,6-Trimethyl-bicyclo[3.1.1]heptane-3-spiro-2'-cyclohexen-4'-one [1] | | 0.00 | 14.02 | 26.00 | 72.64 | 75.94 | 75.68 | | | | |
| Cashmeran | | 0.00 | 0.00 | 19.17 | 54.04 | 71.46 | 70.05 | 73.15 | | 0.60 | |
| Mixture of 9,12-octadecadienoic acid & 9,12,15-octadecatrienoic acid | 54.35 | 69.63 | 79.57 | 84.91 | 100 | 100 | | | 32.00 | 47.00 | |
| Nerolidol | | 0.00 | 6.52 | 53.50 | 56.88 | 68.45 | 66.85 | | | | |
| 1,4-Dioxacyclohexadecane-5,16-dione [5] | | 0.00 | 0.00 | 0.00 | 28.18 | 37.31 | 36.48 | | 3.00 | | |
| Tetrahydromyrcenol | | 0.00 | 0.00 | 0.00 | 0.00 | 41.38 | 72.56 | 66.63 | | | |
| Ambrox ® [5] | | 0.00 | 0.00 | | | | 18.23 | 38.00 | 0.30 | | |
| Terpenyl acetate | | 0.00 | 0.00 | 0.00 | 0.00 | 0.00 | 6.81 | 00.00 | 46.00 | 47.00 | 12.00 |
| 4-tert-Butyl-1-cyclohexanol | | 0.00 | 0.00 | 0.00 | 0.00 | 59.78 | 89.12 | | | | |
| Clove absolute | | 0.00 | 0.00 | 0.00 | 0.00 | 0.00 | 14.00 | 100.00 | | 0.60 | |
| (−)-(1'R,E)-3,3-Dimethyl-5-(2',2',3'-trimethyl-3'-cyclopenten-1'-yl)-4-penten-2-ol [1] | | 0.00 | 27.39 | 75.11 | 76.95 | 76.65 | | | | 0.60 | |
| Essential cedar oil | | 0.00 | 0.00 | 11.23 | 17.00 | 20.00 | | | 1.50 | | |
| 3,5,5-Trimethyl-1-hexanol | | 0.00 | 0.00 | 0.00 | 0.00 | 34.95 | 58.33 | 62.93 | | | |
| Cardamome essential oil | | 0.00 | 0.00 | 0.00 | 0.00 | 25.06 | | | | 0.60 | |
| Orange terpenes | | 0.00 | 0.00 | 0.00 | 0.00 | 32.10 | | | 0.30 | | |
| Patchouli essential oil | | | | | 17.51 | | | | | | 29.00 |

| MOC INGREDIENT | MOC COMPOSITIONS | | | | | | |
|---|---|---|---|---|---|---|---|
| | 4 | 5 | 6 | 7 | 8 | 9 | 10 |
| | (Ingredient concentration w/w %) | | | | | | |
| (−)-(2E)-2-Ethyl-4-[(1R)-2,2,3-trimethyl-3-cyclopenten-1-yl]-2-buten-1-ol [1] | 6.00 | 6.00 | | | | | |
| Bourgeonal [2] | | | | | | | |
| Coranol ® [3] | | | 10.00 | | | 13.00 | |
| Lilial ® [4] | 64.00 | 29.00 | 10.00 | | | | |
| (+)-(1S,2S,3S)-2,6,6-Trimethyl-bicyclo[3.1.1]heptane-3-spiro-2'-cyclohexen-4'-one [1] | | | | | | | 4.00 |
| Cashmeran | | | | | | | |
| Mixture of 9,12-octadecadienoic acid & 9,12,15-octadecatrienoic acid | | | 30.00 | 33.00 | 38.00 | 38.00 | 30.00 |
| Nerolidol | | | | 11.00 | 25.00 | | 35.00 |
| 1,4-Dioxacyclohexadecane-5,16-dione [5] | | 24.00 | 5.00 | 11.00 | 13.00 | 13.00 | |
| Tetrahydromyrcenol | | | 10.00 | | | | |
| Ambrox ® [5] | | | | | | | |
| Terpenyl acetate | | 29.00 | 10.00 | 11.00 | | 13.00 | |
| 4-tert-Butyl-1-cyclohexanol | | | 20.00 | 22.00 | 25.00 | 25.00 | 20.00 |
| Clove absolute | | | | | | | |
| (−)-(1'R,E)-3,3-Dimethyl-5-(2',2',3'- | | | | | | | |

TABLE 1-continued trimethyl-2'-cyclopenten-1'-yl)-4-penten-2-ol [1]
Essential cedar oil
3,5,5-Trimethyl-1-hexanol — 5.00
Cardamome essential oil
Orange terpenes
Patchouli essential oil

[1] Origin: Firmenich SA, Geneva, Switzerland
[2] 3-(4-tert-butylphenyl)propanal; origin: Firmenich SA, Geneva, Switzerland
[3] 4-cyclohexyl-2-methyl-2-butanol; origin: Firmenich SA, Geneva, Switzerland
[4] 3-(4-tert-butylphenyl)-2-methylpropanal; origin: Givaudan SA, Vernier, Switzerland
[5] 8,12-epoxy-13,14,15,16-tetranorlabdane; origin: Firmenich SA, Geneva, Switzerland

TABLE 2

| MOC INGREDIENT | Ingredient Malodor Inhibition Value (%) Concentration in Medium (w/v %) | | | | | | | | MOC COMPOSITIONS I1 I2 I3 I4 (Ingredient concentration w/w %) | | | |
|---|---|---|---|---|---|---|---|---|---|---|---|---|
| | 0.0006 | 0.0012 | 0.0025 | 0.005 | 0.0125 | 0.025 | 0.05 | 0.1 | | | | |
| (E)-2-Dodecenal* | | 10.37 | 29.72 | 55.42 | 86.93 | 94 | | | | | | |
| Mixture of tridecenal & 2-methyldodecanal* | | | 29.11 | 39.43 | 83.49 | | | | | | | |
| 8-Isopropyl-6-methyl-bicyclo[2.2.2]oct-5-ene-2-carbaldehyde* | | | 18.91 | 28.29 | 76.89 | 84.45 | 82.89 | 88.20 | | | | 25 |
| 3-(3-Isopropyl-1-phenyl)butanal* | | | 16.63 | 30.10 | 73.81 | 95.51 | 99.45 | 97.34 | | | | 25 |
| (E)-2-Decenal | | | 21.97 | 28.18 | 66.63 | 90.11 | 100 | | | | | 25 |
| Mixture of 3-(4-methyl-3-pentenyl)-3-cyclohexene-1-carbaldehyde & 4-(4-methyl-3-pentenyl)-3-cyclohexene-1-carbaldehyde | | | 0.00 | 0.00 | 62.75 | 93.89 | 94.75 | | | 25 | 25 | |
| 9-Undecenal* | | | 0.00 | 0.00 | 62.41 | 88.95 | 81.80 | 77.86 | | | 25 | |
| Vetyver Haiti | | | 0.00 | 0.00 | 58.97 | 58.6 | | | | | 25 | |
| Vetyverone | | | 10.9 | 10.40 | 44.6 | | 47.1 | 54.2 | | | | |
| 4,5,6,7,8,9,10,11,12,13-Decahydrocyclododeca-1,3-oxazole | | | 0.00 | 0.00 | 52.20 | | | | | | | 25 |
| 2-Tridecenal (ethyl citrate solution) | | | 28.98 | 40.19 | 50 | 81 | | | | | | 25 |
| 10-Undecenal | | | 3.00 | | 49.2 | | | | 20 | 25 | | |
| Mixture of 10-undecenal & 9-undecenal | | | 8.26 | 2.38 | 49.2 | | | | 20 | | | |
| Nonanal | | | 5.26 | 5.08 | 40.21 | 80.43 | 94.81 | 97.81 | 20 | 25 | | |
| Orris concrete | | | 4.22 | 14.17 | 39.45 | | | | | | | |
| (+)-(4R)-1-P-Menthene-9-carbaldehyde* | | | 0.00 | 3.44 | 34.61 | 81.68 | 97.82 | | | 25 | | |
| (E)-4-Decenal | | | 21.97 | 28.18 | 66.63 | 90.11 | 100 | | | | | |
| 3,7-Dimethyloctanal | | | 0.00 | 0.00 | 18.1 | 66.7 | | | | | | |
| Eucalyptus essential oil | | 37.87 | 72.73 | | | | | | | | | |
| Mixture of 3-(3,3-dimethyl-5-indanyl)propanal & 3-(1,1-dimethyl-5-indanyl)propanal | | | 0.00 | 0.00 | 52 | | | | | | | |
| (Z)-4-Dodecenal | 0.00 | | 0.00 | 6.96 | 76.53 | | | | 20 | | | |
| 3-(6,6-Dimethyl-bicyclo[3.1.1]hept-2-en-2-yl)propanal | | | 0.00 | 4.58 | 82.82 | 96.73 | 100 | 96.35 | 20 | | | |

*Origin: Firmenich SA, Geneva, Switzerland

TABLE 3

| MOC COMPOSITION | Composition Malodor inhibition coefficient (%) Concentration in Medium (v/v %) | | |
|---|---|---|---|
| | 0.025 | 0.0125 | 0.00625 |
| 1 | 100.0 | 86.7 | 31.9 |
| 2 | 87.7 | 92.0 | 52.5 |
| 3 | 89.3 | 81.3 | 44.2 |
| 4 | 84.6 | 81.4 | 48.1 |
| 5 | 64.3 | 57.2 | 18.9 |
| 6 | 76.7 | 71.8 | 48.1 |
| 7 | 62.7 | 70.5 | 39.6 |
| 8 | 64.3 | 73.2 | 48.0 |
| 9 | 78.4 | 66.4 | 43.3 |
| 10 | 70.8 | 85.2 | 45.4 |

TABLE 4

| MOC COMPOSITION | Composition Malodor inhibition coefficient (%) Concentration in Medium (v/v %) | | |
|---|---|---|---|
| | 0.025 | 0.0125 | 0.00625 |
| 11 | 96.97 | 48.56 | 0 |
| 12 | 83.39 | 47.42 | 6.95 |
| 13 | 91.64 | 68.50 | 9.15 |
| 14 | 92.34 | 68.81 | 19.6 |

Example 15

Preparation of Perfuming Compositions Comprising the Malodor Counteracting (MOC) Compositions and Their Use to Reduce Perception of Sweat Malodor Novel perfuming compositions according to the invention were prepared by adding to a reference perfume A of the woody, oriental, spicy type, which showed no malodor reduction capability when tested on its own according to the Protocol A, described in Example 1, a variety of MOC compositions according to the invention, in a number of concentrations.

As is apparent from FIG. 1, the addition of the MOC compositions to perfume A rendered the novel perfumes of the invention very efficient to counteract sweat malodor. FIGS. 1 a) to d) represent the % of malodor inhibition obtained according to Protocol A. of the MOC compositions of the invention, which comprised at least 80% by weight of MOC ingredients according to the invention, when used at varied concentrations in the medium together with perfume A.

In FIGS. 1 a) and b) the concentration of (perfume A+MOC composition) was kept constant at 0.025% v/v in the medium, the relative proportions of perfume A/MOC composition varying from 100:1 to 1:1.

In FIGS. 1 c) and d) the perfume A concentration was kept constant at a value of 0.025% v/v relative to the medium, and the concentration of MOC composition in the latter was varied so as to obtain the concentrations of MOC composition in the medium indicated in the X axis.

When used in the test medium at a concentration of at least 0.015% v/v, relative to the total volume of the test medium, the MOC compositions of the invention provided malodor inhibition coefficients representing a malodor reduction of at least 30%, relative to the activity of the fragrance on its own, and in many cases well above 50%. In the figures, the concentration of MOC composition in the testing medium is indicated on the X axis.

Example 16

Preparation of Perfuming Compositions Comprising the Malodor Counteracting (MOC) Compositions and Their Use to Reduce Perception of Sweat Malodor Novel perfuming compositions according to the invention were prepared by adding to a reference perfume B of the aromatic, citrus, woody type, which showed no malodor reduction capability when tested on its own according to the Protocol A, described in Example 1, a variety of MOC compositions according to the invention, in a number of concentrations.

As is apparent from FIG. 2, the addition of the MOC compositions to perfume B rendered the novel perfumes of the invention very efficient to counteract sweat malodor. FIGS. 2 a) to d) represent the % of malodor inhibition obtained according to Protocol A. of the MOC compositions of the invention, which comprised at least 80% by weight of MOC ingredients according to the invention, when used at varied concentrations in the fragrance.

When used in the test medium at a concentration of at least 0.004% v/v, relative to the total volume of the test medium, the MOC compositions of the invention provided malodor inhibition coefficients representing a malodor reduction of at least 30%, relative to the activity of the fragrance on its own, and in many cases well above 50%. In the figures, the concentration of MOC composition in the medium is indicated on the X axis. The perfume B was used in the test medium at a fixed concentration of 0.025% v/v, whereas the concentration of the MOC composition was varied as indicated in the graphs.

Example 17

Malodor Counteracting (MOC) Effect of Compositions and Their Use to Reduce Perception of Sweat Malodor In Vitro The MOC compositions of the invention were added, at a variety of concentrations, to a conventional spray body antiperspirant product representative of the silicone based antiperspirants, containing a silicone base sold under the tradename Dow Corning 245.

The novel body deodorants thus obtained were tested for their ability to mask or inhibit malodor generated in a medium containing bacterial cells of *Staphylococcus haemolyticus*, grown and incubated in a similar manner as previously described, and following the Protocol B. hereafter.

Protocol B. In-Vitro Malodor Inhibition as Evaluated by a Sensory Panel of Individuals.

This protocol follows the same principle as Protocol A. except that the detection system for measuring the malodor reduction capability of the compositions or products according to the invention is different. In the case of the present protocol the detection is sensorial, carried out by a panel of evaluators, on blind tests.

The Cys-Gly precursor, S-[1-(2-hydroxyethyl)-1-methylbutyl]-L-cysteinylglycine, used at 0.01 mM in the medium, is subject to bacterial transformation both in the absence (blank test) and in the presence of each MOC composition, perfuming composition or deodorant/antiperspirant product according to the invention, depending on which product's malodor reduction activity one wishes to evaluate.

The malodor generated by the bacterial transformation is evaluated olfactively (sensorial evaluation) on a defined scale of malodor intensity.

The bacterial cells of *Staphylococcus haemolyticus* are grown and incubated as previously described in Protocol A. 0.1 Volumes of the final bacterial suspension are added to each test sample (final volume 450 μl).

General Procedure: Test samples: reagents are admixed (product to be tested, precursor and bacterial cell suspension), and the reaction is started by adding the bacterial cell suspension as the last reagent, so as to form the testing medium; the samples are then incubated at 37° C. for 18-20 h. In parallel, two reference samples are prepared: a negative reference consisting of a 3 μg/ml solution of the Cys-Gly precursor in the 0.1 M potassium phosphate buffer at pH 7.5, which has no malodor (malodor intensity value zero), and a positive reference which contains the same amount of Cys-Gly precursor buffer solution, and the bacterial cells of *St. haemolyticus*, but contains no MOC composition or product according to the invention. These positive and negative references are incubated under the same conditions as the test samples, and provide the reference for the maximum malodor value in the scale of evaluation, normally 5 or close to 5.

Once the test samples and references are ready for evaluation, a panel of evaluators is asked to measure the malodor intensity of each of the samples, on a blind test and according to the following scale: 0=imperceptible malodor; 1=very weak malodor; 2=weak malodor; 3=moderate malodor; 4=intense malodor; 5=very intense malodor.

The responses from the various panelists are averaged and corrected statistically for standard deviation, to provide a value of malodor intensity for the test sample, and the two reference samples. The "malodor reduction value" for the test sample is then the difference between the positive reference malodor intensity value and the test sample malodor intensity value.

The antiperspirant samples were tested according to this Protocol B, at a defined volume concentration, relative to the total volume of medium, and the ability of the tested deodorant sample to cover the malodor of the evaluation medium was determined through sensorial evaluation by the panel.

In this manner, novel deodorant samples were prepared by adding MOC composition 9, in a variety of weight concentrations relative to the weight of deodorant spray, and were tested for their ability to cover the medium's malodor—the deodorant on its own, without the MOC composition of the invention, showed no malodor coverage ability (malodor reduction value=0) under the testing conditions indicated.

FIG. 3 shows the results of these tests—it is clear from this figure that the MOC composition 9 according to the invention is capable of reducing the sweat malodor when incorporated in the deodorant product, at concentrations varying from 0.05 to 2% weight, relative to the weight of deodorant. The malodor reduction values of the deodorants according to the invention reached values close to 4, at concentrations of MOC composition close to 1% w/w, relative to the weight of deodorant sample.

Examples 18-19

Malodor Counteracting (MOC) Effect of Compositions and Their Use to Reduce Perception of Human Sweat Malodor In Vitro Antiperspirant (AP) spray samples containing MOC composition 1 described in Example 1, as well as perfume A, were prepared using a variety of MOC composition concentrations, and 0.2% weight of the fragrance, relative to the deodorant weight, added to a conventional AP spray base prepared as described here below. The AP base on its own, and containing the perfuming compositions according to the invention, were then tested as described hereafter for their ability to reduce the malodor perceived.

The human sweat samples were incubated for 18-24 h with a mixture of bacterial strains commonly known to generate axillar malodor, and composed of *S. haemolyticus* and a mixture of *Corynebacterium xerosis* ATCC 373 and *Corynebacterium tuberculostearicum* strains. Sweat malodor samples were thus obtained and subsequently treated with the antiperspirant samples containing the MOC compositions of the invention, and evaluated on a blind test by a panel of individuals. The protocol used is described in detail by M. Troccaz et al. in Chemistry and Biodiversity, 2004, 1, 1022-1034.

Malodor intensity values were attributed via a sensory panel evaluation, on blind tests. The panel used a sensory intensity scale from 1 (no malodor) to 5 (very strong malodor) to assess the deodorant performance after 18 to 24 hours of incubation.

A reference control sample, containing only the mixture of sweat and bacteria cells, was evaluated at the same time, providing a rating for the maximum malodor intensity (5 or close to 5).

A typical antiperspirant spray base was used, comprising the ingredients listed here below on Table 5, in the proportions indicated, the mixture of which was formulated as an aerosol spray by using 25% weight of the AP base suspension and 75% weight of propellants, typically a mixture propane/butane at a pressure of 2.5 bar.

TABLE 5

| AP Spray Base Suspension | |
|---|---|
| Ingredient | Weight (%) |
| Dow Corning 345 Fluid[1] | 51.8 |
| Isopropyl Myristate | 8.75 |
| Silica | 1 |
| Quaternium-18 Hectorite[2] | 3.25 |
| Aluminium Chlorohydrate | 32 |
| Perfume | 3.2 |

[1]Cyclopentasiloxane (and) Cyclohexasiloxane; origin: Dow Corning.
[2]Suspending agent; origin: RHEOX The results of the evaluation tests are shown in FIG. 4, wherein the MOC composition 1 according to the invention is designated simply as MOC 1. It is quite clear from this graph that the deodorant products comprising the MOC and perfuming compositions of the invention can reduce the malodor perception by above 2 units on the scale of 1 to 5 and that the MOC composition 1 of the invention effectively increases the deodorant base's activity, and that of the combination of deodorant base plus Perfume A, masking ability by at least one such unit, when used at appropriate concentrations in the deodorant product.

According to another embodiment, antiperspirant (AP) samples, containing MOC composition 9 described in Example 9, were prepared by using the suspension base described above (without propellant) and a variety of MOC composition concentrations, relative to the deodorant suspension weight. The results of the testing are shown in FIG. 7, which clearly shows that MOC composition 9 significantly reduces the malodor intensity perceived by the panel, even when present at low concentrations in the AP spray suspension base. The latter appears to have no significant malodor reduction capability on its own, whereas when comprising the MOC composition 9 (simply designated as MOC 9 in the graph) it shows a malodor reduction value of up to 2, at MOC 9 weight concentrations of 1% w/w, relative to the weight of the AP base.

Examples 20-21

Malodor Counteracting (MOC) Effect of Compositions and Their Use to Reduce Perception of Sweat Malodor In Vitro MOC composition 1 of the invention was evaluated, according to Protocol B, described in Example 17, for its ability to reduce malodor perceived from the medium, when present in the latter in a variety of concentrations. FIG. 5 shows the results of the panel evaluations. It is clear from this graph that composition 1 is capable of reducing the malodor perceived by the panel, relative to a maximum malodor reference, by a value (malodor reduction value) of about 1.5 to as much as almost 4, depending on its volume concentration in the medium.

Similar tests were carried out, using the same Protocol B described in Example 17, with MOC composition 9 and the results are shown in FIG. 6, again showing great efficacy of the latter to reduce the malodor perceived by the panel, particularly at concentrations of 0.004% v/v and above, relative to the volume of the medium.

Example 22

Malodor Counteracting (MOC) Effect of Composition 1 to Reduce Perception of Sweat Malodor In Vivo, in the Form of a Spray Deodorant According to the Invention A standard deodorant test to measure the efficacy of a deodorant spray containing 0.4% by weight of MOC Composition 1 described in Example 1 was carried out. The deodorant spray composition is described here below. The objective was to demonstrate 5 hour and 24 hour efficacy of the MOC composition.

Alcoholic deodorant spray composition (30% solution/70% Propane-Butane 2.5 bar) for in vivo assay, ingredients and respective concentrations:

| | |
|---|---|
| Ethanol 95° | 86.67% |
| Glyceryl ricinoleate | 1% |
| Caprylic/capric triglyceride | 11% |
| MOC Composition 1 | 1.33% |

A team of three trained panelists between the ages of 20 and 40 years was selected for olfactory evaluation, each of them being able to detect the reduction of body odour, following the application of a deodorant product, on a 0 (no odor) to 5 (very strong odor) linear scale.

A panel of 31 male subjects aged within the range of from 20 to 50 years were denied the use of any type of deodorant or antiperspirant during two weeks before the start of the test, and were assigned a non-deodorant, unperfumed, soap bar for exclusive use of bathing.

On the first day of the test, the body odor of each of the panelists' axillae was assessed by the trained assessors and assigned a score corresponding to the strength of the odor on the scale of 0 to 5. Then the axillae were washed by a technician according to a standardized method, using an unperfumed soap bar, wiped with a water rinsed flannel, and dried with a clean towel.

The deodorants were applied by the technician in a standard application according to an experimental design, whereby each product was applied to the same number of left and right axillae. The panelists then left the test centre.

On the same day there was an additional assessment 5 hours after application to test for 5 hour efficacy. There was no further application of product at this stage.

On the second day panelists attended at the same time, i.e. 24 hours later. The intensity of their body odor was evaluated by all three assessors, they sniffed each axilla and scored for body odor as before. Then the axillae were washed and a second application of product was made.

The assessment and application were repeated on the third and fourth days, and on the fifth day a final assessment was performed.

The body odor scores were averaged and are shown in the Table hereafter.

TABLE

Mean malodor scores after application as described above

| Time after application | Score |
|---|---|
| Just after | 1.99 |
| 5 Hours | 0.97 |
| Day 1 | 1.33 |
| Day 2 | 1.33 |
| Day 3 | 1.08 |
| Day 4 | 0.80 |

After 5 and 24 hours following application of the product according to the invention, there were reductions in mean malodor, significant at the 99.99% confidence level. This showed conclusively that MOC composition 1 gave 24 hour protection against body odor. After continued application for the rest of the week, mean malodor scores continued to fall, suggesting a build-up in efficacy. After 4 days application the reduction in malodor was in the region of about 60% relative to the value immediately after application. The reduction in malodour is about 50% 5 hours after application.

The results above show that the composition according to the invention significantly reduces sweat malodour for more than 24 hours after application, when applied in vivo in the form of a spray deodorant product.

What is claimed is:

1. A composition comprising:
   a 9,12-octadecadienoic acid;
   a 9,12,15-octadecatrienoic acid; and
   3-(4-tert-butylphenyl)propanal; and
   wherein the total concentration of the 9,12-octadecadienoic acid and the 9,12,15-octadecatrienoic acid is at least 50% by weight of the composition; and
   wherein the concentration of 3-(4-tert-butylphenyl)propanal is 5-30% by weight of the composition.

2. A deodorant composition comprising:
   a 9,12-octadecadienoic acid;
   a 9,12,15-octadecatrienoic acid; and
   3-(4-tert-butylphenyl)propanal; and
   wherein the weight ratio of the sum of the 9,12-octadecadienoic acid and the 9,12,15-octadecatrienoic acid to the 3-(4-tert-butylphenyl)propanal is 50:30 to 95:5; and
   wherein the total concentration of the 9,12-octadecadienoic acid, the 9,12,15-octadecatrienoic acid, and the 3-(4-tert-butylphenyl)propanal is 0.3 to 10% by weight of the deodorant composition.

3. An antiperspirant composition comprising:
a 9,12-octadecadienoic acid;
a 9,12,15-octadecatrienoic acid; and
3-(4-tert-butylphenyl)propanal; and
wherein the weight ratio of the sum of the 9,12-octadecadienoic acid and the 9,12,15-octadecatrienoic acid to the 3-(4-tert-butylphenyl)propanal is 50:30 to 95:5; and
wherein the total concentration of the 9,12-octadecadienoic acid, the 9,12,15-octadecatrienoic acid, and the 3-(4-tert-butylphenyl)propanal is 0.3 to 10% by weight of the antiperspirant composition.

4. A body care product comprising at least 0.5% by weight, relative to the total weight of the product, of the composition of claim 1.

5. The body care product of claim 4 wherein the composition is present in an amount of 1 to 5% by weight, relative to the total weight of the product.

6. A body deodorant product comprising at least 0.5% by weight, relative to the total weight of the product, of the composition of claim 1.

7. The body deodorant product of claim 6 wherein the composition is present in an amount of 1 to 5% by weight, relative to the total weight of the product.

8. An antiperspirant product comprising at least 0.5% by weight, relative to the total weight of the product, of the composition of claim 1.

9. The antiperspirant product of claim 8 wherein the composition is present in an amount of 1 to 5% by weight, relative to the total weight of the product.

10. The composition of claim 1, further comprising a perfuming co-ingredient.

11. A perfume, body spray, or cologne comprising the composition of claim 10.

12. A method of counteracting sweat malodor, the method comprising applying to a sweat-generating skin surface the composition of claim 1 or a body-care product comprising at least 0.5% by weight of the composition of claim 1, wherein the body-care product is selected from the group consisting of a perfume, a deodorant, and an antiperspirant.

* * * * *